(12) United States Patent
Adriaenssens et al.

(10) Patent No.: US 10,591,493 B2
(45) Date of Patent: Mar. 17, 2020

(54) CALIXPYRROLE COMPOUNDS AND CREATININE-SELECTIVE ELECTRODES COMPRISING THEM

(71) Applicants: FUNDACIO INSTITUT CATALA D'INVESTIGACIO QUIMICA (ICIQ), Tarragona (ES); INSTITUCIO CATALANA DE RECERCA I ESTUDIS AVANCATS, Barcelona (ES); UNIVERSITAT ROVIRA I VIRGILI, Tarragona (ES)

(72) Inventors: Louis Adriaenssens, Mountain View, CA (US); Pau Ballester, Altafulla (ES); Francisco Javier Andrade, Tarragona (ES); Pascal Blondeau, Tarragona (ES); Francesc Xavier Rius, Tarragona (ES); Tomas De Aquino Guinovart Pavon, Tarragona (ES); Daniel Hernandez Alonso, Malaga (ES)

(73) Assignees: FUNDACIO INSTITUT CATALA D'INVESTIGACIO QUIMICA (ICIQ), Tarragona (ES); INSTITUCIO CATALANA DE RECERCA I ESTUDIS AVANCATS, Barcelona (ES); UNIVERSITAT ROVIRA I VIRGILI, Tarragona (ES)

( * ) Notice: Subject to any disclaimer, the term of this patent is extended or adjusted under 35 U.S.C. 154(b) by 46 days.

(21) Appl. No.: 15/543,151

(22) PCT Filed: Jul. 28, 2015

(86) PCT No.: PCT/EP2015/067241
§ 371 (c)(1),
(2) Date: Jul. 12, 2017

(87) PCT Pub. No.: WO2016/116175
PCT Pub. Date: Jul. 28, 2016

(65) Prior Publication Data
US 2017/0370948 A1    Dec. 28, 2017

(30) Foreign Application Priority Data
Jan. 19, 2015   (EP) .................................. 15382007

(51) Int. Cl.
*G01N 33/00*   (2006.01)
*G01N 33/70*   (2006.01)
(Continued)

(52) U.S. Cl.
CPC .............. *G01N 33/70* (2013.01); *B01J 39/16* (2013.01); *C07D 403/14* (2013.01);
(Continued)

(58) Field of Classification Search
CPC ...................................................... G01N 33/70
(Continued)

(56) References Cited

U.S. PATENT DOCUMENTS

2002/0115566 A1   8/2002  Sessler et al.

OTHER PUBLICATIONS

Wang et al. "Exploring the mechanism of ion-pair recognition by new calix[4]pyrrole bis-phosphonate receptors: insights from quantum mechanics study" RSC Adv., 2014, 4, 1864 (Year: 2014).*

(Continued)

*Primary Examiner* — Christine T Mui
*Assistant Examiner* — Emily R. Berkeley
(74) *Attorney, Agent, or Firm* — Merchant & Gould P.C.

(57) ABSTRACT

Compounds are of the formula (Ia), (Ib), (Ic), or are stereoisomers thereof, wherein: R1 is hydrogen, (C1-C20) alkyl; (C3-C20)alkenyl; (C3 C20)alkynyl; (C1-C6)alkyl-O—; (C3-C20)cycloalkyl; (C1 C20)haloalkyl; (C6-C20)aryl optionally substituted; (C6-C20)heteroaryl optionally substituted; R2 and R2' are hydrogen; (C1-C20)alkyl; (C1-C6)

(Continued)

alkyl-O—; (C1-C6)haloalkyl; halogen; cyano; and nitro; Z1 to Z4 are diradicals of formula (III) wherein A1 and A2 are O— or NR3-, wherein R3 is selected from the group consisting of hydrogen and (C1-C20)alkyl; and G is (C1-C6)alkyl; —P(=S)R5-; —P(=O)R4; —P(=O)(OR4)-; —P(=O)(NR6R7)-; —S(=O)2-; S(=O)—; or —C(=O)—; and Y1 to Y4 are (C1-C8)alkyl; (C3-C7)cycloalkyl; (C6-C20)aryl optionally substituted; or (C6-C20)heteroaryl optionally substituted; and FG1 and FG2 are H, OH, or NHR8.

3 Claims, 3 Drawing Sheets

(51) Int. Cl.
| | |
|---|---|
| C07D 403/14 | (2006.01) |
| C07D 487/22 | (2006.01) |
| B01J 39/16 | (2017.01) |
| C07D 491/22 | (2006.01) |
| C07F 9/6571 | (2006.01) |
| C08J 5/22 | (2006.01) |
| C08K 5/32 | (2006.01) |
| C08K 5/5373 | (2006.01) |
| C08K 5/55 | (2006.01) |
| G01N 27/40 | (2006.01) |

(52) U.S. Cl.
CPC ......... *C07D 487/22* (2013.01); *C07D 491/22* (2013.01); *C07F 9/657181* (2013.01); *C08J 5/22* (2013.01); *C08K 5/32* (2013.01); *C08K 5/5373* (2013.01); *C08K 5/55* (2013.01); *G01N 27/40* (2013.01); *C08J 2327/06* (2013.01)

(58) Field of Classification Search
USPC .......................................................... 436/98
See application file for complete search history.

(56) References Cited

OTHER PUBLICATIONS

Wang et al. "Probing the origin of opposite ion-pair binding behavior for two new calix[4]pyrrole bis-phosphonate receptors" RSC Adv., 2014, 4, 44948 (Year: 2014).*

Galan et al.: "Synthesis, structure, and binding properties of lipophilic cavitands based on a calix[4]pyrrole-resorcinarene hybrid scaffold", J. Org. Chem., 2014, 79, 5545-5557.

Buhlmann et al.: "Influence of Natural, Electrically Neutral Lipids on the Potentiometric Responses of Cation-Selective Polymeric Membrane Electrodes", Analytical Chemistry, vol. 73, No. 14, Jul. 1, 2001 (Jul. 1, 2001), pp. 3199-3205, XP055187023.

Hassan et al: "Novel Biomedical Sensors for Flow Injection Potentiometric Determination of Creatinine in Human Serum", Electroanalysis, vol. 17, No. 24, Dec. 1, 2005 (Dec. 1, 2005), pp. 2246-2253, XP055187013.

Park et al: "Calix[4]pyrroles bearing proximally meso-meso linking straps: synthesis and anion binding properties", Chemical Communications, vol. 48, No. 65, Jan. 1, 2012 (Jan. 1, 2012), p. 8060-8062, XP055186060.

Ciardi et al.: "Switching from Separated to Contact Ion-Pair Binding Modes with Diastereomeric Calix[4]pyrrole Bis-phosphonate Receptors", Journal of the American Chemical Society, vol. 134, No. 31, Aug. 8, 2012 (Aug. 8, 2012), pp. 13121-13132, XP055186304.

Sessler et al.: "Cytosine substituted calix[4]pyrroles: Neutral receptors for 5'-guanosine monophosphate", Proceedings of the National Academy of Sciences, vol. 99, No. 8, Apr. 16, 2002 (Apr. 16, 2002), pp. 4848-4853, XP055216150.

International Search Report and Written Opinion from corresponding International Application No. PCT/EP2015/067241, dated Oct. 15, 2015.

* cited by examiner

CALIXPYRROLE COMPOUNDS AND CREATININE-SELECTIVE ELECTRODES COMPRISING THEM

This application is a National Stage Application of PCT/EP2015/067241, filed 28 Jul. 2015, which claims benefit of Ser. No. 15382007.1, filed 19 Jan. 2015 in Europe and which applications are incorporated herein by reference. To the extent appropriate, a claim of priority is made to each of the above disclosed applications.

BACKGROUND

The present invention relates to the fields of analytical chemistry and medicine. In particular the present invention refers to calixpyrrole compounds useful as ionophores, to membranes, electrodes, and devices including them as well as to methods for determining the amount of creatinine in a test sample using them.

BACKGROUND ART

Creatinine is a normal metabolic by-product generated by the cells. Since its accumulation is toxic, creatinine is transported by the bloodstream to the kidneys to be filtered out and excreted through the urine. For this reason, the levels of creatinine in blood or urine are key parameters used to evaluate proper kidney function. Creatinine levels are used to calculate the glomerular filtration rate (GFR), a magnitude used to assess the performance of the kidneys. The normal levels of creatinine in blood, which depend on age and sex, are well established. High levels of creatinine reflect a disease or a condition affecting the kidneys—such as infections, illnesses, chronic failures, etc.—that may lead from mild to severe health risks, and even death. For example, in chronic kidney failures creatinine levels must be carefully and frequently checked, since they are used to determine when the haemodialysis treatment must be performed. Creatinine clearance is also required before many medical treatments, such as chemotherapy. Additionally, in urine analysis, creatinine is used as normalization factor to minimize the variability due to volume dilution. The literature deals with many more examples where the determination of creatinine in biological fluids and clinical samples is important. All in all, the precise determination of the levels of creatinine in biological fluids, particularly blood and urine, is extremely relevant. For this reason, it is one of the most commonly required determinations in the routine of the clinical laboratories.

Several approaches for the determination of creatinine have been reported. Colorimetric methods are the most widely used. The foundation of most of these methods is based on the Jaffé reaction—described more than a century ago-, which consists in a specific reaction under strong basic conditions between creatinine and picric acid that yields a coloured compound that can be measured colorimetrically at 505 nm. Variations on this method are also used for the routine determination of creatinine in the clinical lab. Other colorimetric methods are based on the use of creatinine amidohydrolase (EC 3.5.2.10).

However, colorimetric methods are not free from interferences. From one side, the response depends strongly on the colour of the sample. Turbidity or highly coloured samples may lead to significant errors. Other molecules that can affect the development of the colour may also act as chemical interferences. For example, it has been demonstrated that substances such as acetone, cefazolin, cefoxitin, ceftiofur and glucose can lead to positive biased results, while acetoacetic acid, bilirubin and lipids can yield a negatively biased values in serum measurements (Jacobs, R. M. et al., 1991). Therefore, although universally used, colorimetric methods are not free of analytical and practical problems.

Today, the gold standard for the determination of creatinine is the isotope dilution gas chromatography-mass spectrometry (ID-GC-MS), since it provides highly accurate results. Nevertheless, this method requires an expensive and complex instrumentation and suitable degree of expertise for the operation. All in all, despite the optimal performance, due to problems associated to cost, simplicity and availability, ID-GC-MS is a good referee method, but it cannot be yet considered a viable routine approach in the clinical laboratory and even less a viable solution for point of care.

In view of the above, several alternative electrochemical methods have been reported in an attempt to develop a viable routine method for determining the level of creatinine. Among them, amperometric biosensors are the most common electrochemical methods so far. These biosensors mainly rely on a three-enzyme method, which involves a three-stage conversion of creatinine to creatine, creatine to sarcosine and sarcosine to glycine. At the end, the generation of $H_2O_2$ produced during the last stage is monitored. This type of approach is common to amperometric systems. Immobilization of these enzymes has been studied for decades, and a portable clinical analyzer called iSTAT® is already in the market where the enzymes are immobilized on cartridges that are commercially available. However, these enzyme-based methods are not free of interferences (Dimeski, C. et al., 2010). Furthermore, the complex combination of enzymes requires careful storage and manipulation of the sensors. It has been disclosed that iSTAT has not shown an appropriate sensitivity for creatinine.

Another electrochemical alternative is based on potentiometric methods, which have become attractive because of their simplicity of operation, robustness, and cost-effectiveness. For this reason, they are ideal tools for point-of-care and other out-of-the-lab measuring approaches. Indirect biosensors for creatinine based on the enzymatic hydrolysis of creatinine and the potentiometric detection of a reaction by-product (pH, ammonium ions, etc) have been described by some researchers, such as Rechnitz (Meyerhoff, M., 1976). However, the use of enzymes makes difficult the storage and conditioning of the analytical devices.

To avoid all these problems associated to the use of enzymes or other biological compounds, direct potentiometric sensors are preferred. In this case, the solution containing creatinine must be adjusted to a suitable pH in order to turn creatinine into the protonated form—the creatininium ion. Bühlmann and co-workers introduced an ionophore-free ion-selective electrode by incorporating chloroparaffin as plasticizer for the direct determination of creatinine. This sensor shows good performance in synthetic samples. However, when dealing with the determination of creatinine in real samples, they observed a serious fouling coming from electrically neutral lipids that affected the measurements (Bühlmann, P., 2001) and hindered the applications. To reduce this biofouling, a polymeric membrane with fluorinated compounds was proposed. However, the selectivity obtained using these approaches is not enough for the determination of creatinine in real samples. To improve the selectivity of potentiometric sensors, the best approach is to use synthetic receptors (ionophores) to entrap creatinine using host-guest based chemistry. Few macromolecules have been reported so far as new receptors for creatinine. Nevertheless, none of them meets the analytical performance (such as limit of detection, stability, selectivity coefficients, among others) required for the determination of creatinine in real samples (Hassan, S. S. M., 2005).

In summary, all the methods used nowadays in routine analysis for the determination of creatinine suffer from drawbacks in the analytical performance, related in particular to selectivity, re-usability, accuracy and ease of implementation (portability). Alternative approaches reported up to date in the literature, such as potentiometric sensors, fail to meet the analytical performance required to be applied in real samples.

Therefore, there is still the need of sensors able of detecting selectively creatinine which can alleviate many current problems in the clinical laboratories and open new opportunities in fields such as telemedicine and point of care diagnosis.

The state of the art discloses many calixpyrroles. In Ballester P et al., 2012 there are disclosed stereoisomers of the calix[4]pyrroles:

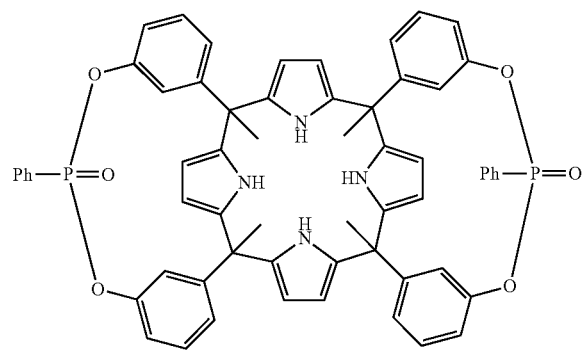

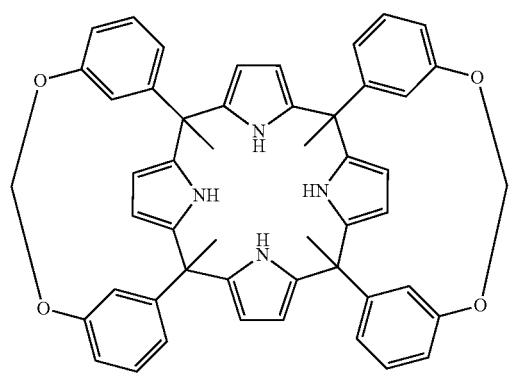

In addition, Galán A. et al., discloses the calix[4]pyrrole:

(VI)

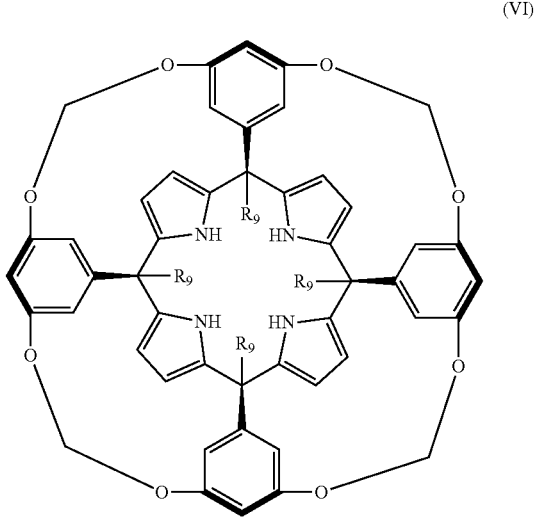

where $R_9$ is $C_{12}H_{23}$.

SUMMARY OF THE INVENTION

The present inventors have developed new calixpyrrole compounds which are useful as creatinine ionophores. As shown below, when a calixpyrrole such as those disclosed herein is used as ionophore in the manufacture of a sensor, it is found that the resulting sensor shows high selectivity for creatinine in front of other ions (interferences) present in real samples. Therefore, the use of this novel ionophores minimizes the drawbacks produced by typical interferences, such as $K^+$.

In Buhlman et al., 2001, wherein the use of membranes with a specific polymeric matrix composition is used, there was the need for changes on said polymeric matrix composition in order to get some selectivity for creatinine. However, these membranes showed biofouling problems and could not be used in the detection of creatinine in real samples because they were not selective enough.

The present inventors have found that using the compounds of the present invention as ionophores in the manufacture of a membrane, it is observed a minimization of the biofouling as well as a long-term stability of the electrode. FIG. 1 is illustrative of the fact that the compounds of the invention provide good sensitivity, since they allow the detection of the analyte at very low concentrations.

The findings provided by the present inventors means a great advance in the field of clinical analysis because it is the first time that an ionophore can be formulated in a membrane for the potentiometric detection of creatinine in a real sample, the membrane meeting the analytical performance, such as limit of detection, stability, selectivity coefficients, among others (see Table 3 below) required for the determination of creatinine in real samples.

The fact that the compounds of the present invention confer to sensors the selectivity and usability in potentiometric methods means a great advance in the clinical analysis because (a) the determination is performed in a fast and simple way since no special treatment of the sample is required prior to the determination and no special reagents (such as enzymes) are necessary in the detection; (b) the required volume of sample is very low; (c) the materials needed for the potentiometric method are cheap (the support of the membrane can be a paper sheet for instance); (d) as not being required the use of enzymes, it is stable so it can be stored for long periods of time.

Thus, in a first aspect, the present invention provides a compound of formula (Ia), or alternatively (Ib) or alternatively (Ic), or any of the stereoisomers of (Ia), (Ib) or (Ic)

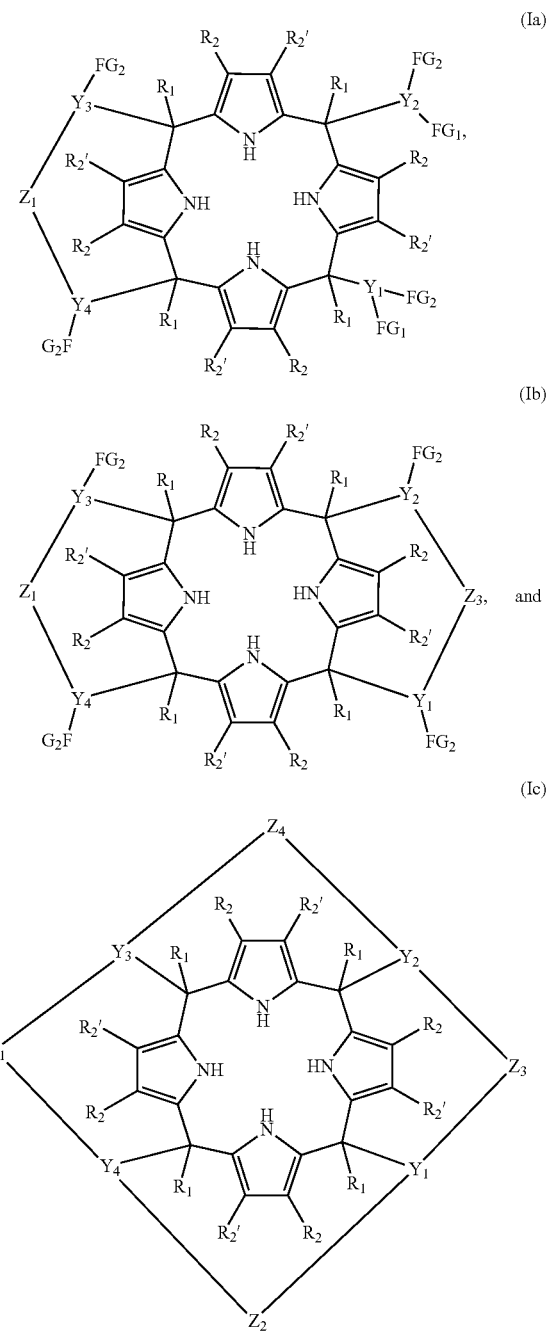

wherein
$R_1$ is a monoradical selected from the group consisting of hydrogen; $(C_1-C_{20})$alkyl; $(C_3-C_{20})$alkenyl; $(C_3-C_{20})$alkynyl; $(C_1-C_6)$alkyl-O—; $(C_1-C_{20})$haloalkyl; $(C_6-C_{20})$aryl; $(C_6-C_{20})$aryl substituted with one or more radicals independently selected from $(C_1-C_{20})$alkyl, $(C_1-C_6)$alkyl-O—, $(C_1-C_6)$haloalkyl, halogen, cyano, and nitro; $(C_6-C_{20})$heteroaryl; and $(C_6-C_{20})$heteroaryl substituted with one or more radicals independently selected from $(C_1-C_{20})$alkyl, $(C_1-C_6)$alkyl-O—, $(C_1-C_6)$haloalkyl, halogen, cyano, and nitro;

$R_2$ and $R_2'$ are monoradicals each one being independently selected from the group consisting of hydrogen, $(C_1-C_{20})$alkyl, $(C_1-C_6)$alkyl-O—, $(C_1-C_6)$haloalkyl, halogen, cyano, and nitro;

$Z_1$ to $Z_4$ are diradicals of formula (III)

wherein $A_1$ and $A_2$ are independently selected from the group consisting of —O— and —$NR_3$—, wherein $R_3$ is selected from the group consisting of hydrogen and $(C_1-C_{20})$alkyl; and G is a diradical selected from the group consisting of —$NH_2$, —P(=S)($R_5$), —S(=O)$_2$—, $(C_1-C_6)$alkyl, —S(=O)—, —C(=O)—, —P(=O)($R_4$)—, —P(=O)($NR_6R_7$)— and —P(=O)($OR_4$);

$R_4$ and $R_5$ are monoradicals independently selected from the group consisting of $(C_1-C_{20})$alkyl; $(C_3-C_8)$cycloalkyl; $(C_2-C_{20})$alkenyl; $(C_3-C_{20})$cycloalkyl; $(C_1-C_{20})$haloalkyl; $(C_1-C_{20})$alkyl-O—; $(C_6-C_{20})$aryl; $(C_6-C_{20})$heteroaryl; $(C_6-C_{20})$ aryl substituted with one or more radicals independently selected from $(C_1-C_{20})$alkyl, $(C_1-C_6)$haloalkyl, $(C_1-C_6)$alkyl-O—, halogen, cyano, nitro; and $(C_6-C_{20})$heteroaryl substituted with one or more radicals independently selected from $(C_1-C_{20})$alkyl, $(C_1-C_6)$alkyl-O—, $(C_1-C_6)$haloalkyl, halogen, cyano, and nitro;

$Y_1$ to $Y_4$ are triradicals each one independently selected from the group consisting of $(C_1-C_8)$alkyl; $(C_3-C_7)$cycloalkyl; $(C_6-C_{20})$aryl; $(C_6-C_{20})$aryl substituted with one or more radicals independently selected from the group consisting of: $(C_1-C_{20})$alkyl, $(C_1-C_6)$alkyl-O—, $(C_1-C_6)$haloalkyl, halogen, cyano, and nitro; $(C_6-C_{20})$heteroaryl; and $(C_6-C_{20})$ heteroaryl substituted with one or more radicals independently selected from the group consisting of: $(C_1-C_{20})$alkyl, $(C_1-C_6)$alkyl-O—, $(C_1-C_6)$haloalkyl, halogen, cyano, and nitro;

$R_6$ and $R_7$ are monoradicals independently selected from the group consisting of —H and $(C_1-C_{20})$alkyl;

$FG_1$ and $FG_2$ are monoradicals independently selected from the group consisting of H, OH, and $NHR_8$ wherein $R_8$ is a radical selected from the group consisting of hydrogen and $(C_1-C_{20})$alkyl;

wherein
$(C_6-C_{20})$aryl represents a C— radical of a ring system from 6 to 20 carbon atoms, the system comprising from 1 to 3 rings, where each one of the rings forming the ring system: is saturated, partially unsaturated, or aromatic; and is isolated, partially fused or totally fused;

$(C_6-C_{20})$heteroaryl represents a C— radical of a ring system from 6 to 20 members, the system comprising from 1 to 3 rings, wherein at least one of the rings contains from one to four heteroatoms independently selected from O, S and N, and wherein each one of the rings forming the ring system: is saturated, partially unsaturated or aromatic; and is isolated, partially fused or totally fused; and $(C_3-C_{20})$cycloalkyl refers to a saturated carbocyclic ring system from 3 to 20 carbon atom members, the system comprising from 1 to 3 rings;

provided that the compound of formula (Ib) is other than a compound of formula (IV) and stereoisomers thereof, or (V) and stereoisomers thereof, and provided that the compound of formula (Ic) is other than a compound of formula (VI):

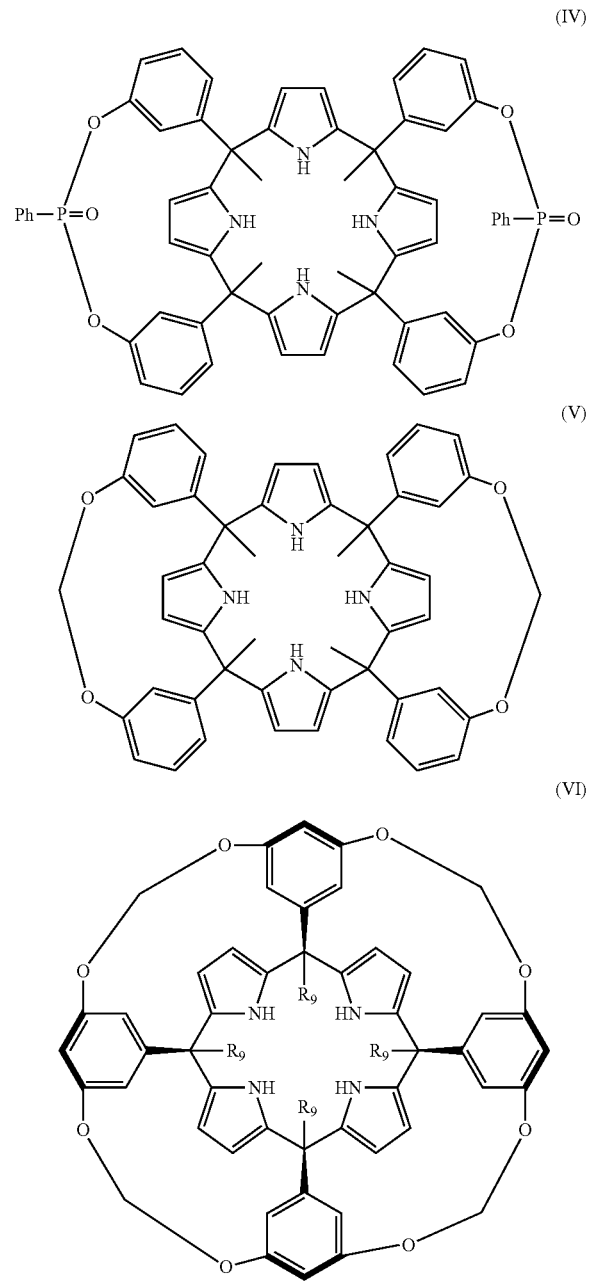

wherein $R_9$ is $C_{12}H_{23}$.

Without being bound to the theory, it is believed that the selectivity for creatinine is due to the common calixpyrrole structure having at least one bridge formed by members —Y—Z—Y—, this bridge forming a ring connecting the two non-adjacent carbon atoms to which $R_1$ radicals are attached.

As mentioned above, the compounds of formula (Ia), (Ib), or (Ic), or a stereoisomer thereof of the present invention can be incorporated into a suitable membrane which, as shown in the experimental data, is selective to creatininium ions.

Thus, in a second aspect the present invention provides a membrane comprising: (i) a compound of formula (Ia), (Ib), or (Ic), or a compound of formula (IV), (V), or a stereoisomer thereof, as defined above or a compound of formula (VI), (ii) a polymeric matrix; (iii) a plasticizer; and (iv) a cation-exchanger salt.

The suitable combination of all these elements (i) to (iv) produces an ion-selective membrane for the detection of creatinine which, by proper adjustment of the pH of the sample, allows the fast, selective and sensitive determination of creatinine in real samples such as urine and plasma. As shown in Example 12 below and FIGS. 1 and 2, the sensor exhibits an almost Nernstian response (54.2±0.6 mV/log aCreatinine), a linear range from $10^{-6}$ M to $10^{-2}$ M of creatinine, and limits of detection typically in the range of $10^{-6.2}$ M of creatinine In a third aspect the present invention provides an electrode comprising the membrane as defined above.

As shown in FIG. 1 the compounds of the present invention show a short response time (when the addition of a creatinine solution was added to the medium, the electrode lasted about 10 seconds in giving the new measure of potential) and good stability because the potential signal is kept continue and constant until the addition of a new solution of creatinine at a different concentration. In addition, from FIG. 2 it can be concluded that when a sensor comprising a compound of the invention is used, there is a Nernstian response, which means that there is a linear relationship between the creatinine concentration and the signal and that, therefore, the sensor works adequately. In fact, from FIG. 2 it can be concluded that including a compound of the invention, the sensor is able of detecting concentrations of the order of $10^{-6}$, whereas the same membrane without such compound does not. From FIG. 2 it can also be concluded, therefore, that the inclusion of a compound of the invention confers to the sensor an appropriate sensitivity to creatinine. In view of the above, the inclusion of a compound of the invention in a sensor allows the simple and fast determination of creatinine in clinical samples, such as plasma and urine, with minimal sample manipulation.

In a fourth aspect the present invention provides a device comprising the electrode of the third aspect of the invention.

As it has been mentioned above, the compounds of the present invention allows the specific detection of creatinine ions in a test sample. Consequently, these compounds are useful in the routine determination of creatinine levels in any test sample.

Therefore, in a fifth aspect the present invention provides a method for the quantification of a creatinine in an isolated test sample comprising the step of (a) contacting the test sample with a membrane, electrode or device as defined in any of the previous aspects; and (b) correlating the potential value with the amount of creatinine comprised in the sample.

In a further aspect the present invention provides a process for preparing a compound of formula (Ia), (Ib), (Ic), or a stereoisomer thereof as defined above, wherein:

(a) when the compound is one of formula (Ia), the process comprises the reaction between a compound of formula (VII) with a compound of formula (VIII), wherein the molar ratio between the compound (VII) with respect to the compound (VIII) is comprised from 1:1 to 1:2, the reaction being performed in a basic medium

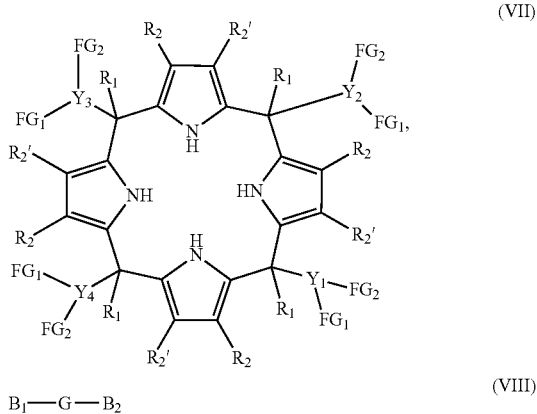

(VII)

B₁—G—B₂ (VIII)

wherein $R_1$, $R_2$, $R_2'$, $FG_1$, $FG_2$, $Y_1$ to $Y_4$, and G are as defined above, and $B_1$ and $B_2$ are radicals independently selected from the group consisting of halogen, tosylate, triflate, nonaflate and imidazole;
(b) when the compound is one of formula (Ib), the process comprises:
b.1. the reaction between a compound of formula (VII) with the compound of formula (VIII) as defined above, being the compound of formula (VII) in a molar ratio with respect to the compound of formula (VIII) comprised from 1:2 to 1:10, the reaction being performed in a basic medium; or alternatively,
b.2. the reaction between a compound of formula (Ia) with the compound of formula (VIII) as defined above, being the compound of formula (Ia) with respect to compound of formula (VIII) in a molar ratio comprised from 1:1 to 1:6, the reaction being performed in a basic medium;
(c) when the compound is one of formula (Ic), the process comprises:
c.1. the reaction between a compound of formula (VII) with the compound of formula (VIII) as defined above, being the compound of formula (VII) with respect to the compound of formula (VIII) in a molar ratio comprised from 1:4 to 1:10, the reaction being performed in a basic medium; or alternatively,
c.2. the reaction between a compound of formula (Ia) with the compound of formula (VIII) as defined above, being the compound of formula (Ia) with respect to the compound of formula (VIII) in a molar ratio comprised from 1:3 to 1:10, the reaction being performed in a basic medium; or alternatively,
c.3. the reaction between a compound of formula (Ib) with the compound of formula (VIII) as defined above, being the compound of formula (Ib) with respect to the compound of formula (VIII) in a molar ratio comprised from 1:2 to 1:10, the reaction being performed in a basic medium.

As it has been mentioned above, the compounds of the invention are highly selective for creatinine, so when they are formulated in membrane and are placed in contact with the test sample, they selectively "trap" creatinine at the interface between the solution and the membrane. The experimental data provided below supports the fact that the sensor is selective for creatinine, even at low concentrations. This is indicative that the compounds of the invention are receptors specific for creatinine. This is indicative of the usability of the compounds of the invention as ionophore.

Therefore, in a further aspect the invention provides the use of a compound of formula (Ia), (Ib), or (Ic) as defined above thereof as ionophore.

Ballester P et al., 2012 and Galan A. et al., 2014 do not disclose that the calix[4]pyrroles disclosed therein can be used as ionophores specific for creatinine.

Therefore, in a further aspect the invention provides the use of a compound of formula (Ia), (Ib), or (Ic) or of a compound of formula (IV), (V), or a stereoisomer thereof or a compound of formula (VI) as ionophore specific for creatinine.

Finally, as it has been mentioned previously, creatinine is widely used as biomarker of several disorders. Since the compounds of the present invention show high selectivity for creatinine, they can be useful, either alone or formulated in the form of a membrane, electrode, or device, as a diagnostic/prognostic tool in creatinine-disease related disorders.

In a last aspect the present invention provides the use of a compound of formula (Ia), (Ib), or (Ic) as defined above, or of a compound of formula (IV), (V), or a stereoisomer thereof or a compound of formula (VI) for use in diagnostics or prognosis.

DETAILED DESCRIPTION OF THE INVENTION

Figure 1:
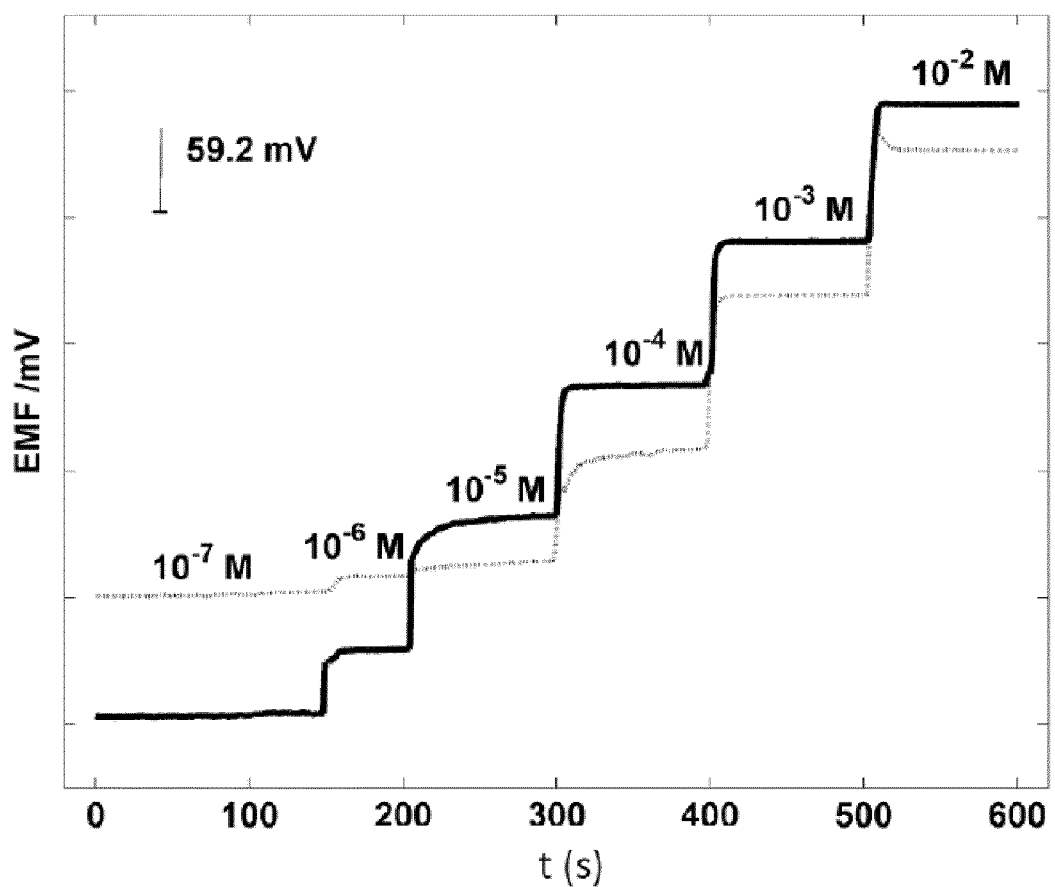
FIG. 1 shows the whole potentiometric time—trace up to levels of 10 mM of creatinine. Y-axis=potential (mV), X-axis=time (seconds). The solid line corresponds to the response of the creatinine ion-selective electrode described in this invention. The grey line corresponds to the unspecific response using a sensor built without ionophore. This figure illustrates the clear influence of the creatinine receptor to improve the limit of detection as well as to expand the working range of the sensor.

All terms as used herein in this application, unless otherwise stated, shall be understood in their ordinary meaning as known in the art. Other more specific definitions for certain terms as used in the present application are as set forth below and are intended to apply uniformly throughout the specification and claims unless an otherwise expressly set out definition provides a broader definition.

The calixpyrroles disclosed in the present invention show an isomerism when the "Z" dirradical comprises a G selected from —P(=O)($R_4$)—, —P(=O)(O$R_4$)—, —P(=O)(N$R_6R_7$)—, and —P(=S)($R_5$)—, in such a way that the radical(s) composing G radical point either inside the structure ("in") or outside ("out"). For instance, if G radical is a —P(=O)R$_4$, the oxygen radical can be inside the structure (thus being R$_4$ outside), or oxygen can be outside the structure (thus being R$_4$ inside). This same applies to the other G radicals —P(=O)(OR$_4$)—, —P(=O)(NR$_6$R$_7$)—, and —P(=S)(R$_5$)—.

As mentioned above, the present invention provides new compounds of formula (Ia), (Ib), or (Ic) useful as creatinine ionophores.

In the present invention, the term "alkyl" refers to a linear or branched hydrocarbon chain which contains the number of carbon atoms specified in the description or the claims. Examples include, among others, methyl, ethyl, propyl, isopropyl, butyl, isobutyl, pentyl, hexyl, octyl, heptyl, nonanyl, decanyl, undecanyl, dodecanyl, and tert-butyl.

In the present invention the term "alkenyl" refers to a branched or linear alkyl chain which contains the number of carbon atoms specified in the description or claims and that also contains one or two double bonds. Examples include, among others, ethenyl, 1-propen-1-yl, 1-propen-2-yl, 3-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and dodecenyl.

The term "alkynyl" refers to refers to a branched or linear alkyl chain which contains the number of carbon atoms specified in the description or claims and that also contains one or two triple bonds.

In the present invention, the term "haloalkyl" refers to a linear or branched hydrocarbon chain which contains the number of carbon atoms specified in the description or the claims, wherein at least one of the hydrogen atoms is replaced by an halogen atom selected from F, Cl, L, and Br.

According to the present invention a ring system formed by "isolated" rings means that the ring system is formed by two, three or four rings and said rings are bound via a bond from the atom of one ring to the atom of the other ring. The term "isolated" also embraces the embodiment in which the ring system has only one ring. Illustrative non-limitative examples of known ring systems consisting of one ring are those derived from: cyclopropyl, cyclobutyl, cyclopentyl, cyclohexyl, cycloheptyl, cyclopropenyl, cyclobutenyl, cyclopentenyl, phenyl, biphenylyl, and cycloheptenyl.

According to the present invention when the ring system has "totally fused" rings, it means that the ring system is formed by two, three or four rings in which two or more atoms are common to two adjoining rings. Illustrative non-limitative examples are 1,2,3,4-tetrahydronaphthyl, 1-naphthyl, 2-naphthyl, anthryl, or phenanthryl.

According to the present invention when the ring system is "partially fused", it means that the ring system is formed by three or four rings, being at least two of said rings totally fused (i.e. two or more atoms being common to the two adjoining rings) and the remaining ring(s) being bound via a bond from the atom of one ring to the atom of one of the fused rings.

In one embodiment of the first aspect of the invention:
R$_1$ is a monoradical selected from the group consisting of hydrogen; (C$_1$-C$_{20}$)alkyl; (C$_3$-C$_{20}$)alkenyl; (C$_3$-C$_{20}$)alkynyl; (C$_1$-C$_6$)alkyl-O—; (C$_1$-C$_{20}$)haloalkyl; (C$_6$-C$_{20}$)aryl; (C$_6$-C$_{20}$)aryl substituted with one or more radicals independently selected from (C$_1$-C$_{20}$)alkyl, (C$_1$-C$_6$)alkyl-O—, (C$_1$-C$_6$)haloalkyl, halogen, cyano, and nitro; (C$_6$-C$_{20}$)heteroaryl; and (C$_6$-C$_{20}$)heteroaryl substituted with one or more radicals independently selected from (C$_1$-C$_{20}$)alkyl, (C$_1$-C$_6$)alkyl-O—, (C$_1$-C$_6$)haloalkyl, halogen, cyano, and nitro;

R$_2$, and R$_2$' are monoradicals each one being independently selected from the group consisting of hydrogen, (C$_1$-C$_{20}$)alkyl, (C$_1$-C$_6$)alkyl-O—, (C$_1$-C$_6$)haloalkyl, halogen, cyano, and nitro; and G is a diradical selected from the group consisting of —S(=O)$_2$—, (C$_1$-C$_6$)alkyl, —S(=O)—, —C(=O)—, —P(=O)(R$_4$)—, —P(=O)(NR$_6$R$_7$)—, and —P(=O)(OR$_4$)—, being R$_4$, R$_6$, and R$_7$ as defined above.

In another embodiment of the first aspect of the invention, G is a diradical selected from the group consisting of —P(=S)(R$_5$), —S(=O)$_2$—, (C$_1$-C$_6$)alkyl, —S(=O)—, —C(=O)—, —P(=O)(R$_4$)—, —P(=O)(NR$_6$R$_7$)— and —P(=O)(OR$_4$), being R$_4$, R$_5$, R$_6$ and R$_7$ as defined in the first aspect of the invention.

In another embodiment of the first aspect of the invention, G is a diradical selected from the group consisting of —S(=O)$_2$—, (C$_1$-C$_6$)alkyl, —S(=O)—, —C(=O)—, —P(=O)(R$_4$)—, —P(=O)(NR$_6$R$_7$)— and —P(=O)(OR$_4$)—, being R$_4$, R$_5$, R$_6$ and R$_7$ as defined in the first aspect of the invention.

In another embodiment of the first aspect of the invention, Y$_1$ to Y$_4$ are the same. In another embodiment of the first aspect of the invention, Y$_1$ to Y$_4$ are selected from the group consisting of: (C$_6$-C$_{20}$)aryl; and (C$_6$-C$_{20}$)aryl substituted with one or more radicals independently selected from the group consisting of: (C$_1$-C$_{20}$)alkyl, (C$_1$-C$_6$)alkyl-O—, (C$_1$-C$_6$)haloalkyl, halogen, cyano, and nitro. In another embodiment Y$_1$ to Y$_4$ are C$_6$-C$_{20}$ aryl. In another embodiment Y$_1$ to Y$_4$ are phenyl.

In another embodiment of the first aspect of the invention, radicals FG$_1$ and FG$_2$ are —OH. In another embodiment of the first aspect of the invention FG$_1$ and FG$_2$ are in meta position. In another embodiment, radicals FG$_1$ and FG$_2$ are —OH and are in meta position.

In another embodiment of the first aspect of the invention, Z$_1$ to Z$_4$ radicals are diradicals of formula (III) as defined above, wherein A$_1$ and A$_2$ are the same. In another embodiment, Z$_1$ to Z$_4$ radicals are diradicals of formula (III) as defined above wherein A$_1$ and A$_2$ are —O— diradicals.

In another embodiment of the first aspect of the invention, G is —P(=O)(NR$_6$R$_7$)—, being R$_6$ and R$_7$ as defined above.

In another embodiment of the first aspect of the invention wherein A$_1$ and A$_2$ are the same and represent —O— diradicals, G is —P(=O)(NR$_6$R$_7$)—, and R$_6$ and R$_7$ are as defined above. In another embodiment, R$_6$ and R$_7$ are the same. In another embodiment R$_6$ and R$_7$ are hydrogen.

In another embodiment of the first aspect of the invention, G is —S(=O)$_2$—. In another embodiment of the first aspect of the invention wherein A$_1$ and A$_2$ are the same and represent —O— diradicals, G is —S(=O)$_2$—.

In another embodiment of the first aspect of the invention G is —P(=O)(R$_4$)—, being R$_4$ as defined above.

In another embodiment of the first aspect of the invention wherein A$_1$ and A$_2$ are the same and represent —O— diradicals, G is —P(=O)(R$_4$)—, being R$_4$ as defined above.

In another embodiment of the first aspect of the invention G is —P(=S)(R$_5$)—, being R$_5$ as defined above.

In another embodiment of the first aspect of the invention wherein A$_1$ and A$_2$ are the same and represent —O— diradicals, G is —P(=S)(R$_5$)—, being R$_5$ as defined above.

In another embodiment of the first aspect of the invention R$_4$ is selected from the group consisting of: (C$_1$-C$_{20}$)alkyl, (C$_6$-C$_{20}$)aryl, and (C$_6$-C$_{20}$)aryl substituted as defined above. In another embodiment, R$_4$ is (C$_6$-C$_{20}$)aryl, and (C$_6$-C$_{20}$)aryl substituted as defined above. In another embodiment R$_4$ is a (C$_6$-C$_{20}$)aryl radical. In another embodiment, R$_4$ is selected from the group consisting of: phenyl, tolyl, mesitylenyl, naphthyl, bipheynylyl, quinolinyl N-oxide, quinolinyl N-sulfide and anthracenyl. In another embodiment $R_4$ is a phenyl radical.

In another embodiment of the first aspect of the invention $R_5$ is selected from the group consisting of: $(C_1-C_{20})$alkyl, $(C_6-C_{20})$aryl, and $(C_6-C_{20})$aryl substituted as defined above. In another embodiment, $R_5$ is $(C_6-C_{20})$aryl, and $(C_6-C_{20})$aryl substituted as defined above. In another embodiment $R_5$ is a $(C_6-C_{20})$aryl radical. In another embodiment, $R_5$ is selected from the group consisting of: phenyl, tolyl, mesitylenyl, naphthyl, bipheynylyl, quinolinyl N-oxide, quinolinyl N-sulfide and anthracenyl. In another embodiment $R_5$ is a phenyl radical.

In another embodiment of the compound of the first aspect of the invention, G is a $(C_1-C_{20})$alkyl. In another embodiment G is selected from the group consisting of: methylene, ethylene, propylene, and butylene. In another embodiment G is methylene diradical.

In another embodiment of the compound of the first aspect of the invention, G is —POR$_4$—, wherein $R_4$ is $(C_6-C_{20})$aryl radical, or alternatively G is —PSR$_5$—, wherein $R_5$ is $(C_6-C_{20})$aryl radical, or alternatively G is a $(C_1-C_{20})$alkyl, or alternatively —S(=O)$_2$—, or alternatively —P(=O)(NR$_6$R$_7$)—, wherein $R_6$ and $R_7$ are hydrogen.

In another embodiment of the compound of the first aspect of the invention, G is —POR$_4$—, wherein $R_4$ is $(C_6-C_{20})$aryl radical, or alternatively G is a $(C_1-C_{20})$alkyl, or alternatively —S(=O)$_2$—, or alternatively —P(=O)(NR$_6$R$_7$)—, wherein $R_6$ and $R_7$ are hydrogen.

In another embodiment of the compound of the first aspect of the invention $Z_1$ to $Z_4$ are independently selected from the group consisting of: —O—P(=O)(Ph)-O—, —O—P(=S)(Ph)-O—, —O—P(=O)(NH$_2$)—, —O—S(=O)$_2$—O—, and —O—CH$_2$—O—. In another embodiment of the compound of the first aspect of the invention $Z_1$ to $Z_4$ are independently selected from the group consisting of: —O—P(=O)(Ph)-O—, —O—P(=O)(NH$_2$)—, —O—S(=O)$_2$—O—, and —O—CH$_2$—O—. In another embodiment of the compound of the first aspect of the invention $Z_1$ to $Z_4$ are independently selected from the group consisting of: —O—P(=O)(Ph)-O—, and —O—CH$_2$—O—. In another embodiment of the compound of the first aspect of the invention $Z_1$ to $Z_4$ are independently selected from the group consisting of: —O—P(=O)(Ph)-O—, —O—P(=S)(Ph)-O— and —O—CH$_2$—O—. In another embodiment of the compound of the first aspect of the invention $Z_1$ to $Z_4$ are independently selected from the group consisting of: —O—P(=O)(Ph)-O— and —O—CH$_2$—O—. In another embodiment of the compound of the first aspect of the invention $Z_1$ to $Z_4$ are —O—P(=O)(Ph)-O—. In another embodiment of the compound of the first aspect of the invention $Z_1$ to $Z_4$ are —O—P(=S)(Ph)-O—. In another embodiment of the compound of the first aspect of the invention $Z_1$ to $Z_4$ are —O—CH$_2$—O—.

In another embodiment of the compound of the first aspect of the invention $Z_1$ to $Z_4$ are independently selected from the group consisting of: —O—P(=O)(Ph)-O—, —O—P(=O)(NH$_2$)—, —O—S(=O)$_2$—O—, and —O—CH$_2$—O—. In another embodiment of the compound of the first aspect of the invention $Z_1$ to $Z_4$ are independently selected from the group consisting of: —O—P(=O)(Ph)-O— and —O—H$_2$—O—. In another embodiment of the compound of the first aspect of the invention $Z_1$ to $Z_4$ are —O—P(=O)(Ph)-O—. In another embodiment of the compound of the first aspect of the invention $Z_1$ to $Z_4$ are —O—CH$_2$—O—.

In another embodiment of the compound of the first aspect of the invention, $R_2$ and $R_2'$ are independently selected from the group consisting of H, $(C_1-C_{20})$alkyl, $(C_1-C_6)$alkyl-O—, and halogen. In another embodiment $R_2$ and $R_2'$ are the same. In another embodiment $R_2$ and $R_2$ are H.

In another embodiment of the compound of the first aspect of the invention $R_1$ is selected from the group consisting of: $(C_1-C_{20})$alkyl, $(C_3-C_{20})$alkenyl, $(C_3-C_{20})$alkynyl, and $(C_1-C_{20})$haloalkyl. In one embodiment the alkenyl and alkynyl have the double and triple bond, respectively, at the end of the carbon chain.

In another embodiment $R_1$ is $(C_1-C_{20})$alkyl. In another embodiment $R_1$ is selected from the group consisting of: methyl, ethyl, propyl, and butyl. In another embodiment $R_1$ is methyl. In another embodiment $R_1$ is dodecanyl. In another embodiment $R_1$ is dodecenyl.

In another embodiment the compound of formula (Ia), (Ib), or (Ic) is selected from the group consisting of:

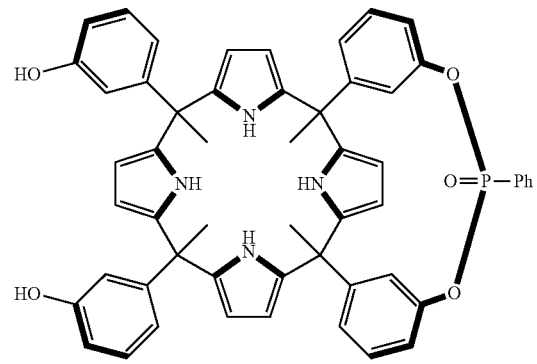

(Ia1)

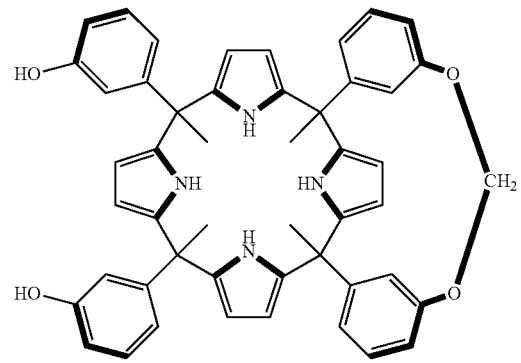

(Ia2)

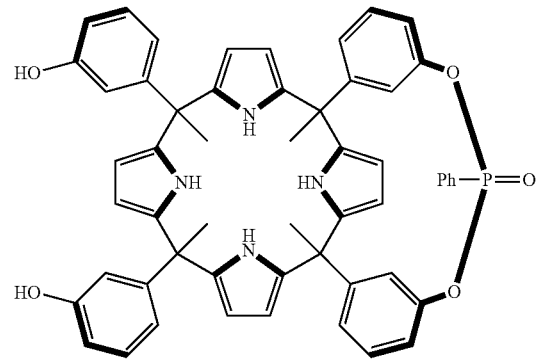

(Ia3)

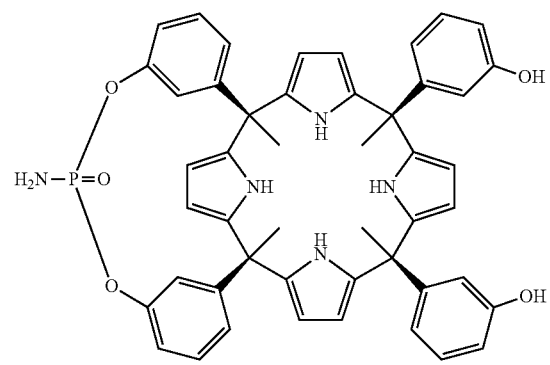
(Ia4)
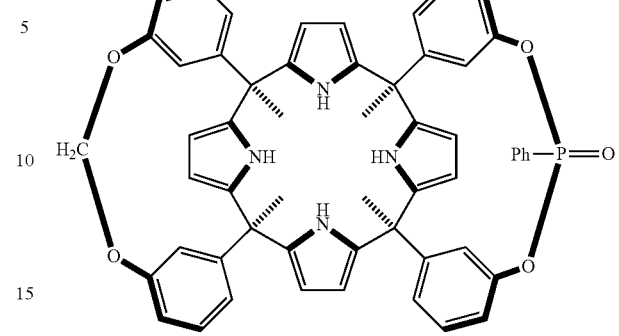
(Ib2)
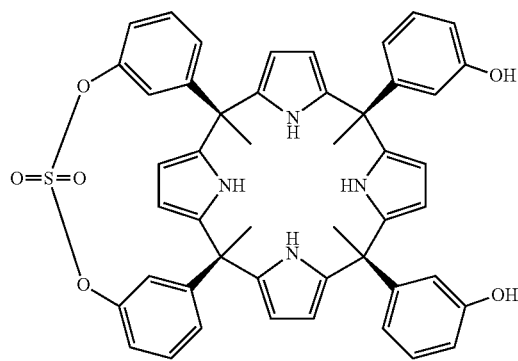
(Ia5)
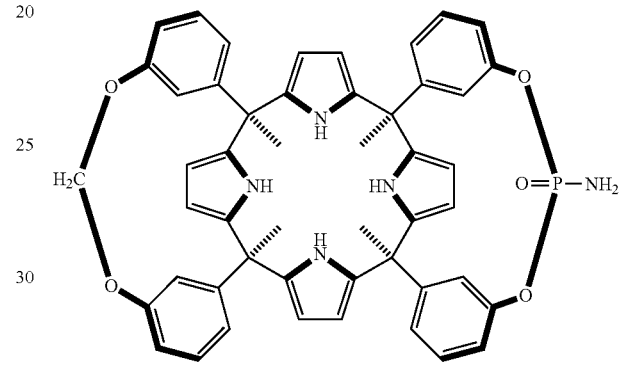
(Ib3)
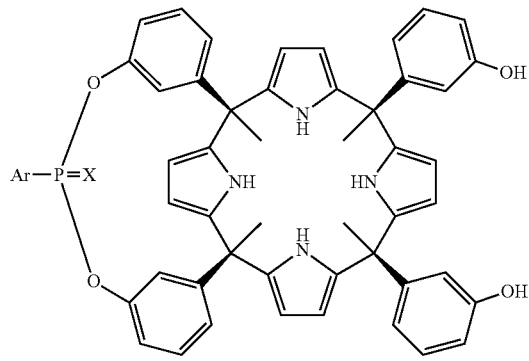
(Ia6)
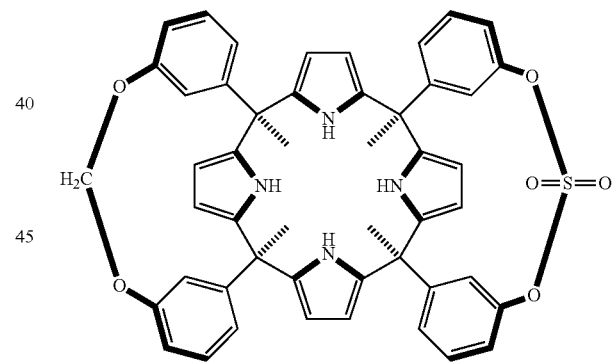
(Ib4)
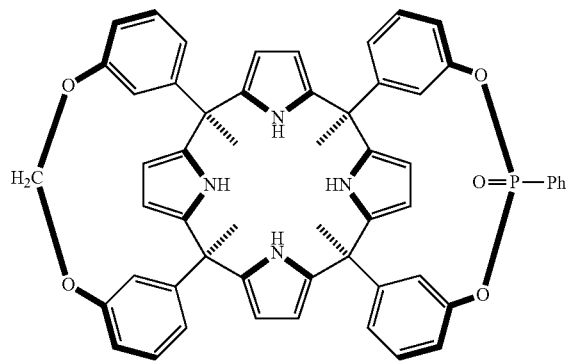
(Ib1)
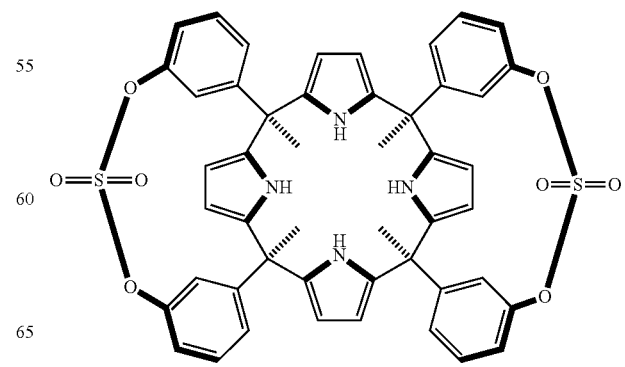
(Ib5)

(Ib6)
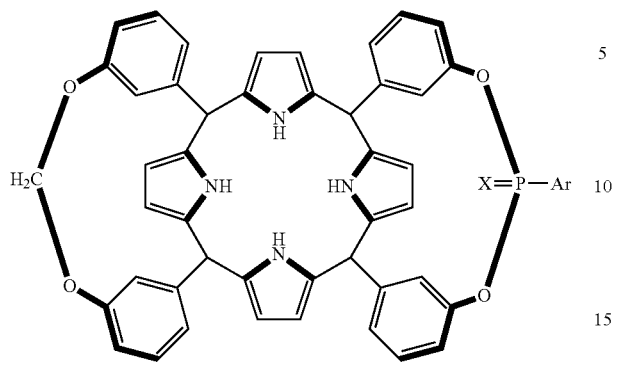
(Ib10)
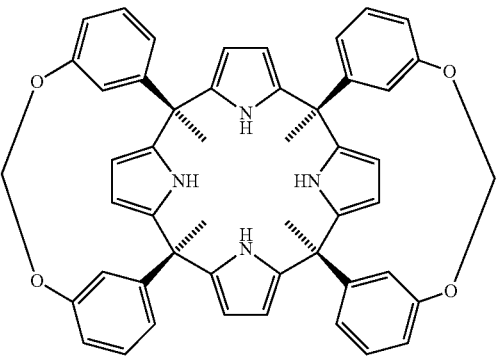
(Ib7)
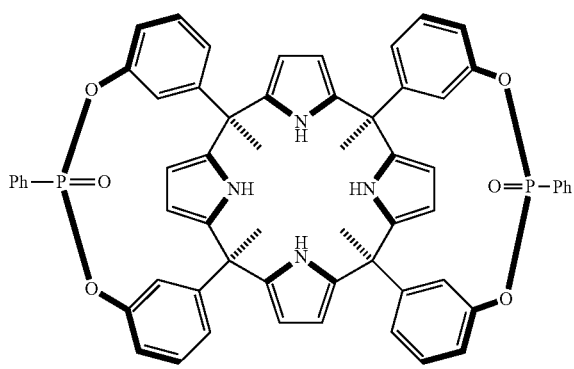
(Ib11)
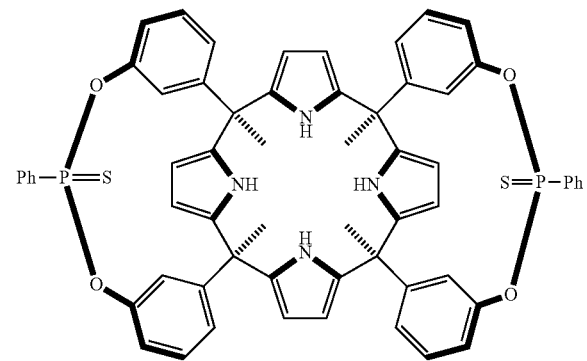
(Ib8)
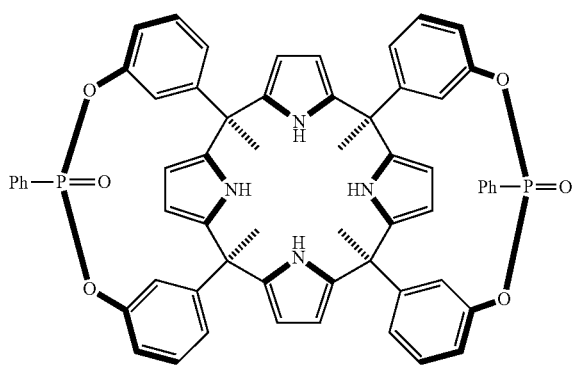
(Ib12)
(Ib9)
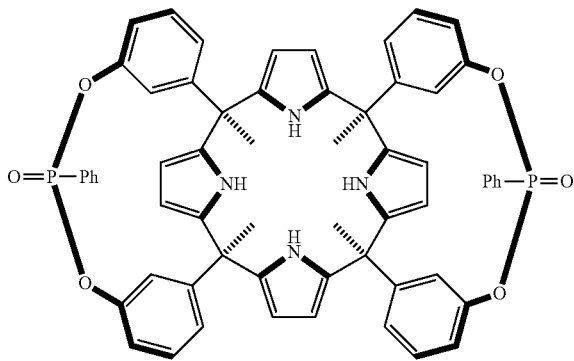
(Ib13)
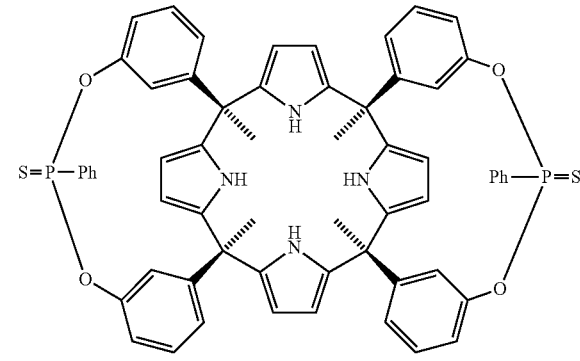

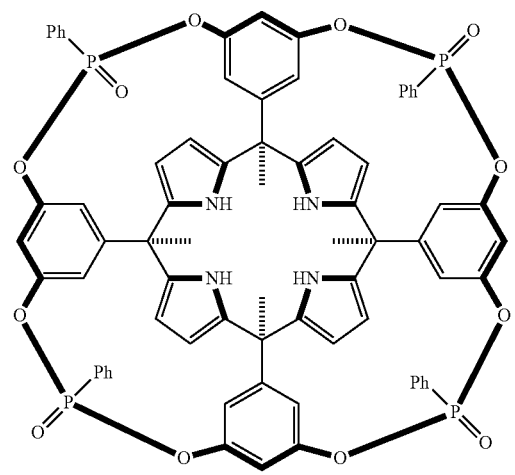
(Ic1)

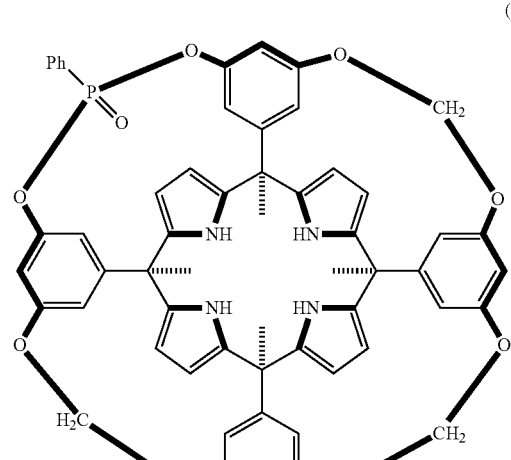
(Ic2)

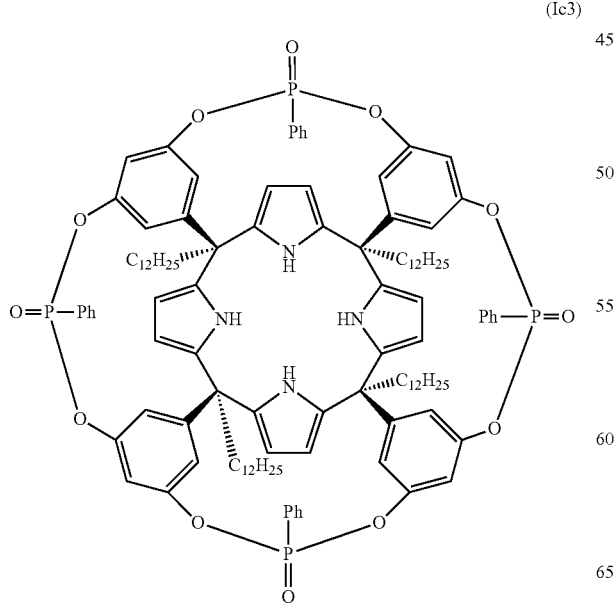
(Ic3)

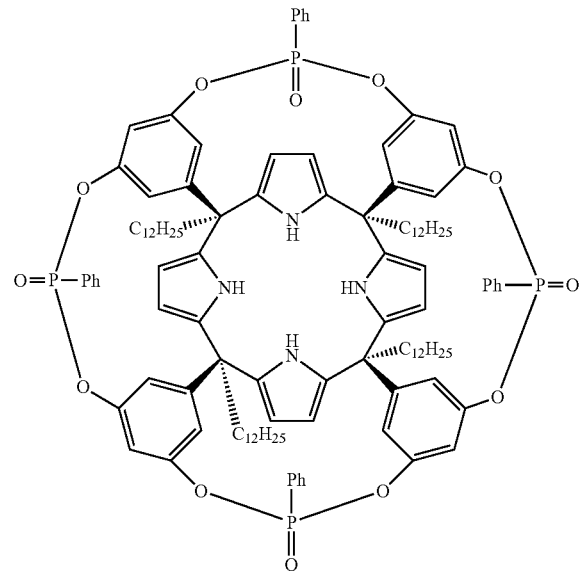
(Ic4)

and a stereoisomer thereof; wherein in the compound of formula (Ia6) and (Ib6): X means O or S; and Ar means tolyl, mesitylenyl, naphthyl, bipheynylyl, quinolinyl N-oxide, quinolinyl N-sulfide and anthracenyl. In another embodiment Ar means mesitylene, naphthalene, and anthracene.

In another embodiment of the first aspect of the invention the compound is selected from the group consisting of:

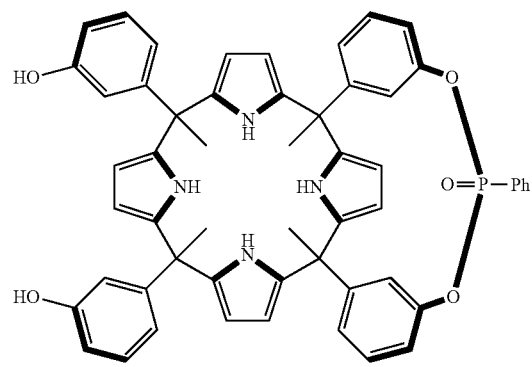
(Ia1)

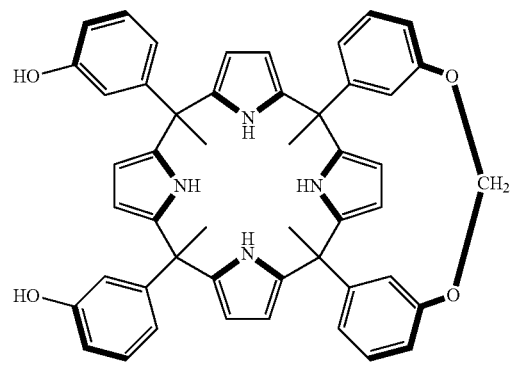
(Ia2)

(Ia3)
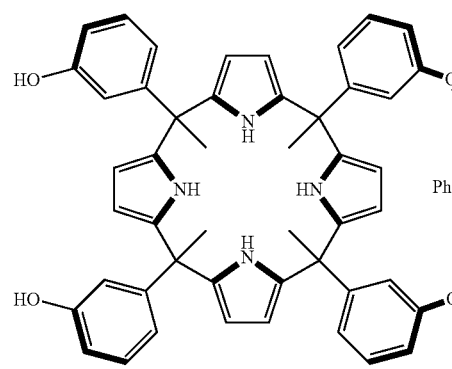
(Ib1)
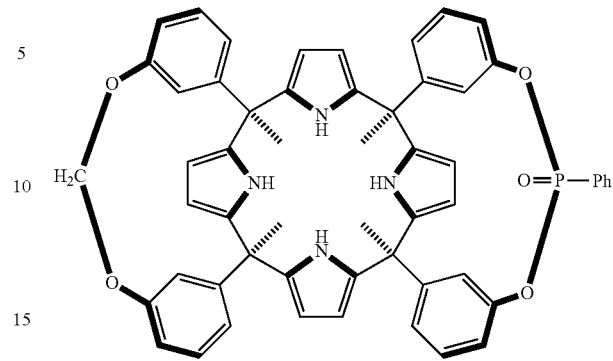
(Ia4)
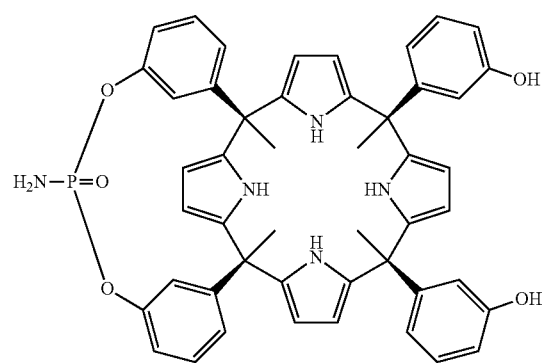
(Ib2)
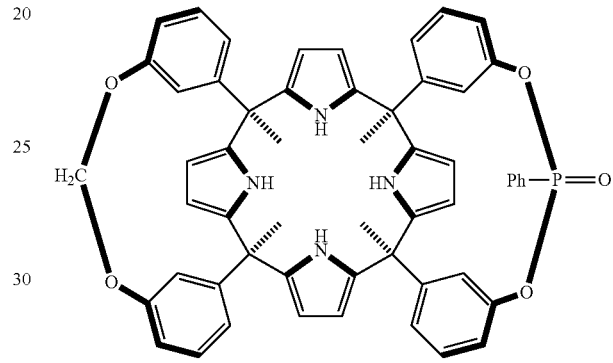
(Ia5)
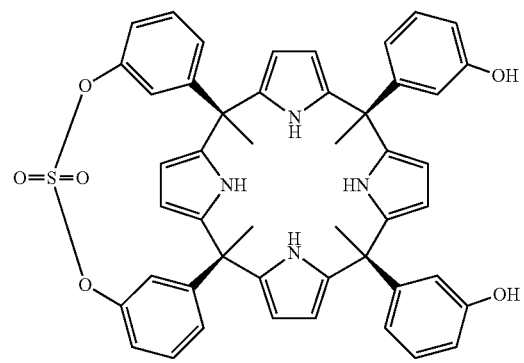
(Ib3)
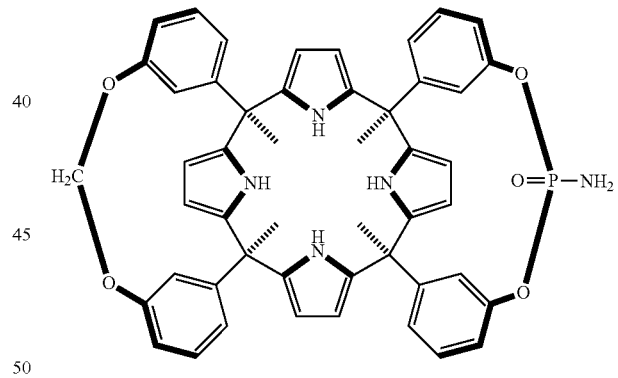
(Ia6)
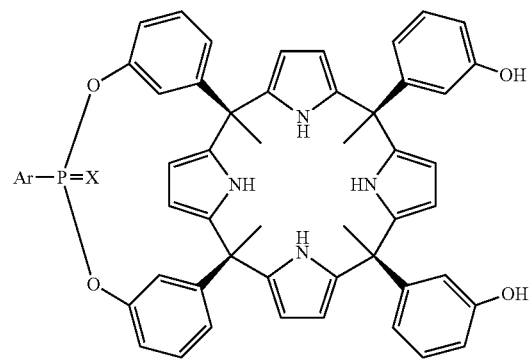
(Ib4)
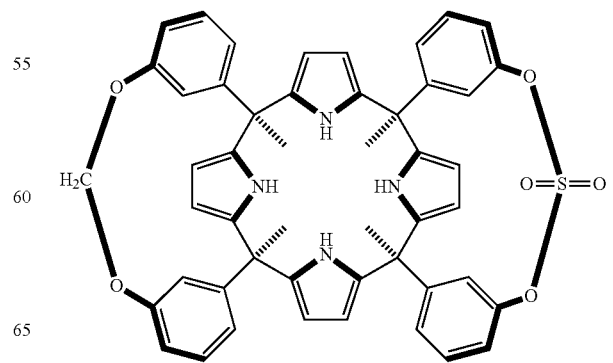

(Ib5)

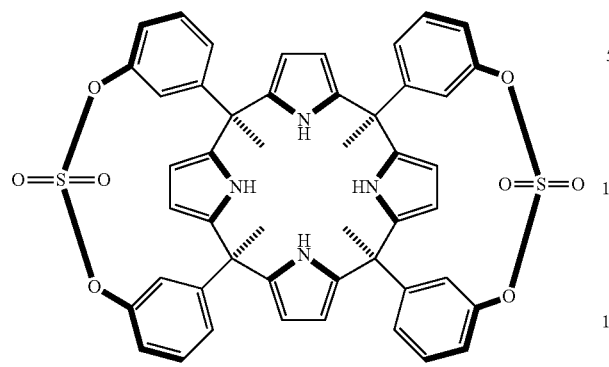

(Ib6)

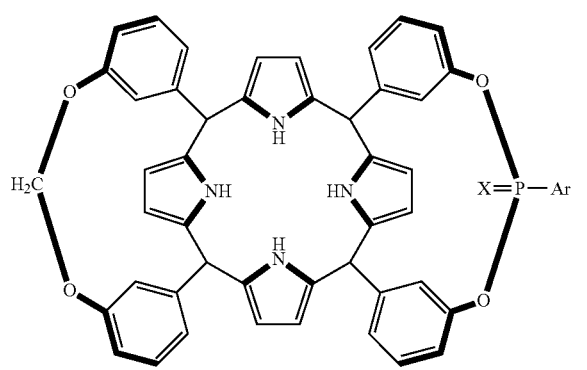

(Ib10)

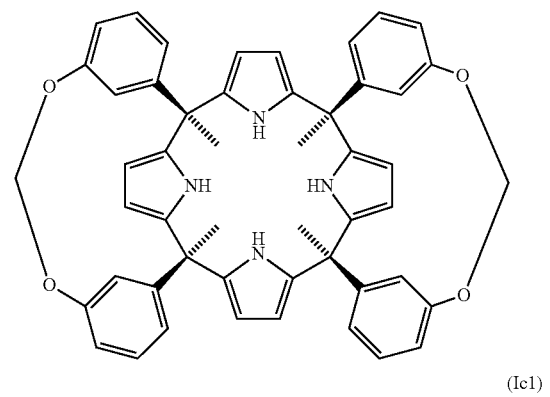

(Ic1)

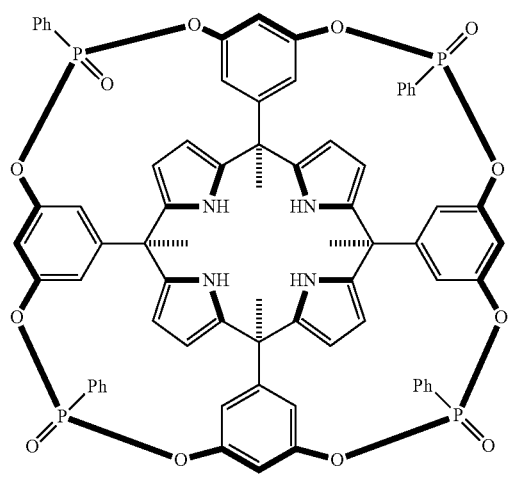

(Ic2)

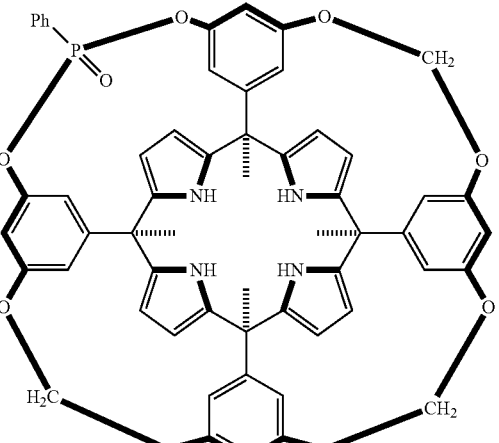

and a stereoisomer thereof; wherein in the compound of formula (Ia6) and (Ib6): R means a $(C_1-C_6)$alkyl; X means O or S; and Ar means mesitylene, naphthalene, and anthracene.

In another embodiment of the first aspect of the invention the compound is selected from the group of compounds consisting of: compound of formula (Ia1), compound of formula (Ia2), compound of formula (Ia3), compound of formula (Ib1), compound of formula (Ib2), compound of formula (Ib7), compound of formula (Ib8), compound of formula (Ib9), compound of formula (Ib10), compound of formula (Ib11), compound of formula (Ib12), compound of formula (Ib13), compound of formula (Ic1), compound of formula (Ic3), compound of formula (Ic4), and a stereoisomer thereof.

In another embodiment of the first aspect of the invention the compound is selected from the group consisting of the compounds of formula: (Ia1), (Ib1), (Ib7), (Ib8), (Ib9), (Ib10), (Ib11), (Ib12), (Ib13), (Ic3), (Ic4), and a stereoisomer thereof. In still another embodiment the compound is selected from the compound of formula (Ia1), compound of formula (Ib1), compound of formula (Ib7), compound of formula (Ib8), compound of formula (Ib9), compound of formula (Ib13), compound of formula (Ic3), and compound of formula (Ic4).

In another embodiment of the first aspect of the invention the compound is selected from the group of compounds consisting of: compound of formula (Ia1), compound of formula (Ia2), compound of formula (Ia3), compound of formula (Ib1), compound of formula (Ib2), and compound of formula (Ic1), and a stereoisomer thereof.

In one embodiment, the compound of the first aspect of the invention is one of formula (Ia). In one embodiment, the compound of formula (Ia) is one wherein $Z_1$ is a diradical of formula (II) as defined above, wherein $A_1$ and $A_2$ are the same. In another embodiment $A_1$ and $A_2$ are —O— diradicals. In one embodiment of the compound of formula (Ia), G is —S(=O)$_2$—. In another embodiment of the compound (Ia), G is —P(=O)(R$_4$)— being R$_4$ as defined above. In another embodiment R$_4$ is selected from the group consisting of: $(C_1-C_{20})$alkyl, $(C_6-C_{20})$aryl, and $(C_6-C_{20})$aryl substituted as defined above. In another embodiment of the compound (Ia), R$_4$ is selected from $(C_6-C_{20})$aryl, and $(C_6-C_{20})$aryl substituted as defined above. In another embodiment R$_4$ is a $(C_6-C_{20})$aryl radical. In another embodiment of the compound (Ia), $R_4$ is selected from the group consisting of: phenyl, tolyl, mesitylenyl, naphthyl, bipheynylyl, quinolinyl N-oxide, quinolinyl N-sulfide and anthracenyl. In another embodiment of the compound (Ia), $R_4$ is a phenyl radical. Alternatively, the compound of formula (Ia) is one wherein G is a $(C_1-C_{20})$alkyl. In another embodiment of the compound (Ia), G is selected from the group consisting of: methylene, ethylene, propylene, and butylene. In another embodiment of the compound (Ia), G is a methylene diradical. Alternatively, in another embodiment of the compound of formula (Ia), G is —P(=O)($NR_6R_7$)—, and $R_6$ and $R_7$ are as defined above. In another embodiment of the compound of formula (Ia), $R_6$ and $R_7$ are the same. In another embodiment of the compound of formula (Ia) $R_6$ and $R_7$ are hydrogen. In another embodiment of the compound of formula (Ia) $Z_1$ is selected from the group consisting of: —O—P(=O)(Ph)-O—, —O—P(=O)($NH_2$)—O—, —O—S(=O)$_2$—O—, and —O—$CH_2$—O—. In another embodiment of the compound of formula (Ia) $Y_1$ to $Y_4$ are the same and are selected from the group consisting of: $(C_6-C_{20})$aryl; and $(C_6-C_{20})$aryl substituted with one or more radicals independently selected from the group consisting of: $(C_1-C_{20})$alkyl, $(C_1-C_6)$alkyl-O—, $(C_1-C_6)$haloalkyl, halogen, cyano, and nitro. In another embodiment $Y_1$ to $Y_4$ are $(C_6-C_{20})$aryl. In another embodiment of the compound (Ia), $Y_1$ to $Y_4$ are phenyl. In another embodiment of the compound (Ia), radicals $FG_1$ and $FG_2$ are —OH. In another embodiment of the compound of formula (Ia) $FG_1$ and $FG_2$ are in meta position. In another embodiment of the compound of formula (Ia) radicals $FG_1$ and $FG_2$ are —OH and are in meta position. In another embodiment of the compound of formula (Ia) $R_2$ and $R_2$' are hydrogen. In another embodiment of the compound of formula (Ia) $R_1$ is $(C_1-C_{20})$alkyl. In another embodiment of the compound of formula (Ia) $R_1$ is selected from methyl, ethyl, propyl, isopropyl, and tert-butyl. In another embodiment of the compound of formula (Ia) $R_1$ is methyl. In another embodiment, $A_1$ and $A_2$ are —O— diradicals; G is —P(=O)($R_4$)— or $(C_1-C_6)$alkyl; $R_4$ is a $(C_6-C_{20})$aryl radical; $Y_1$ to $Y_4$ are the same and are $(C_6-C_{20})$aryl; $FG_1$ and $FG_2$ are —OH and are in meta position; $R_2$ and $R_2$' are hydrogen; and $R_1$ is $(C_1-C_{20})$alkyl. In another embodiment, $A_1$ and $A_2$ are —O— diradicals; G is —P(=O)($R_4$)— or $(C_1-C_6)$alkyl; $R_4$ is a $(C_6-C_{20})$aryl radical; $Y_1$ to $Y_4$ are the same and are phenyl; $FG_1$ and $FG_2$ are —OH and are in meta position; $R_2$ and $R_2$' are hydrogen; and $R_1$ is $(C_1-C_{20})$alkyl. In another embodiment, the compound of formula (Ia) is selected from the compounds of formula (Ia1), (Ia2), (Ia3), (Ia4), and (Ia5) and a stereoisomer thereof. In another embodiment, the compound of formula (Ia) is selected from the compounds of formula (Ia1), (Ia2), (Ia3), and a stereoisomer thereof.

In another embodiment, the compound of the first aspect of the invention is one of formula (Ib). In one embodiment of the compound of formula (Ib), $Z_1$ and $Z_3$ are diradicals independently selected from the group consisting of: —O—P(=O)($R_4$)—O—, —N($R_3$)—P(=O)($R_4$)—N($R_3$)—, —N($R_3$)—P(=O)($R_4$)—O—, —O—P(=S)($R_5$)O—, —N($R_3$)—P(=S)($R_5$)N($R_3$)—, —N($R_3$)—P(=S)($R_5$)—O—, —N($R_3$)—S(=O)$_2$—N($R_3$)—, —N($R_3$)—S(=O)$_2$—O—, —O—S(=O)$_2$—O—, —O—$(C_1-C_6)$alkyl-O—, —O—$(C_1-C_6)$alkyl-N($R_3$)—, —N($R_3$)—$(C_1-C_6)$alkyl-N($R_3$)—, and —P(=O)($NR_6R_7$)—, wherein $R_5$ is a radical selected from the group consisting of: phenyl, tolyl, mesitylenyl, naphthyl, bipheynylyl, quinolinyl N-oxide, quinolinyl N-sulfide and anthracenyl, and $R_3$, and $R_4$ are as defined above, and $R_6$ and $R_7$ are as defined above. In another embodiment of the compound of formula (Ib), $Z_1$ and $Z_3$ are independently selected from —O—P(=S)($R_5$)O—, —O—P(=O)($R_4$)—O—, —O—$(C_1-C_6)$alkyl-O—, and —P(=O)($NR_6R_7$)—. In another embodiment of the compound of formula (Ib), $Z_1$ and $Z_3$ are independently selected from —O—P(=O)($R_4$)—O—, —O—$(C_1-C_6)$alkyl-O—, and —P(=O)($NR_6R_7$)—. In another embodiment of the compound of formula (Ib), $Z_1$ and $Z_3$ are the same. In another embodiment of the compound of formula (Ib), $Z_1$ and $Z_3$ are the same and are selected from —O—P(=S)($R_5$)O—, —O—P(=O)($R_4$)O— and —O—$(C_1-C_6)$alkyl-O—, wherein $R_4$ and $R_5$ are as defined above. In another embodiment of the compound of formula (Ib), $Z_1$ and $Z_3$ are the same and are selected from —O—P(=O)($R_4$)O— and —O—$(C_1-C_6)$alkyl-O—, wherein $R_4$ is as defined above. In another embodiment $R_4$ is selected from the group consisting of: $(C_1-C_{20})$alkyl, $(C_6-C_{20})$aryl, and $(C_6-C_{20})$aryl substituted as defined above. In another embodiment of the compound (Ib), $R_4$ is selected from $(C_6-C_{20})$aryl, and $(C_6-C_{20})$aryl substituted as defined above. In another embodiment $R_4$ is a $(C_6-C_{20})$aryl radical. In another embodiment of the compound (Ib), $R_4$ is selected from the group consisting of: phenyl, tolyl, mesitylenyl, naphthyl, bipheynylyl, quinolinyl N-oxide, quinolinyl N-sulfide and anthracenyl. In another embodiment of the compound (Ib), $R_4$ is a phenyl radical. In another embodiment of the compound of formula (Ib), $Z_1$ and $Z_3$ are —O—P(=O)(Ph)-O—. In another embodiment of the compound of formula (Ib), $Z_1$ and $Z_3$ are —O—$CH_2$—O—. In another embodiment of the compound of formula (Ib), $Z_1$ and $Z_3$ are —O—P(=S)(Ph)-O—. In another embodiment of the compound of formula (Ib) $Z_1$ and $Z_3$ are different. In another embodiment of the compound of formula (Ib) one of $Z_1$ and $Z_3$ is —O—P(=O)($R_4$)—O—. In another embodiment of the compound of formula (Ib), one of $Z_1$ and $Z_3$ is —O—P(=O)($R_4$)—O— or —O—$(C_1-C_6)$alkyl-O—, and the other Z diradical is selected from the group consisting of: —N($R_3$)—P(=O)($R_4$)—N($R_3$)—, —N($R_3$)—P(=O)($R_4$)—O—, —O—P(=S)($R_5$)—O—, —N($R_3$)—P(=S)($R_5$)—N($R_3$)—, —N($R_3$)—P(=S)($R_5$)—O—, —N($R_3$)—S(=O)$_2$—N($R_3$)—, —N($R_3$)—S(=O)$_2$—O—, —O—S(=O)$_2$—O—, —O—$(C_1-C_6)$alkyl-O—, —O—$(C_1-C_6)$alkyl-N($R_3$)—, —N($R_3$)—$(C_1-C_6)$alkyl-N($R_3$)—, and —P(=O)($NR_6R_7$)—, being $R_3$, $R_4$, $R_5$, $R_6$ and $R_7$ as defined above. In another embodiment of the compound of formula (Ib), one of $Z_1$ and $Z_3$ is —O—P(=O)($R_4$)—O— and the other Z diradical is —O—$(C_1-C_6)$alkyl-O—, being $R_4$ as defined above. In another embodiment of the compound of formula (Ib), one of $Z_1$ and $Z_3$ is —O—P(=O)($R_4$)—O—, the other Z diradical is —O—$(C_1-C_6)$alkyl-O—, and $R_4$ is selected from the group consisting of: $(C_1-C_{20})$alkyl, $(C_6-C_{20})$aryl, and $(C_6-C_{20})$aryl substituted as defined above. In another embodiment of the compound (Ib), $R_4$ is selected from $(C_6-C_{20})$aryl, and $(C_6-C_{20})$aryl substituted as defined above. In another embodiment of the compound of formula (Ib), one of $Z_1$ and $Z_3$ is —O—P(=O)($R_4$)—O—, the other Z diradical is —O—$(C_1-C_6)$alkyl-O—, and $R_4$ is a $(C_6-C_{20})$aryl radical. In another embodiment of the compound (Ib), one of $Z_1$ and $Z_3$ is —O—P(=O)($R_4$)—O—, the other Z diradical is —O—$(C_1-C_6)$alkyl-O—, and $R_4$ is selected from the group consisting of: phenyl, tolyl, mesitylenyl, naphthyl, bipheynylyl, quinolinyl N-oxide, quinolinyl N-sulfide and anthracenyl. In another embodiment of the compound (Ib), one of $Z_1$ and $Z_3$ is —O—P(=O)($R_4$)—O—, being $R_4$ are a phenyl radical, and the other Z diradical is —O—$(C_1-C_6)$alkyl-O—. In another embodiment of the compound (Ib), one of $Z_1$ and $Z_3$ is —O—P(=O)($R_4$)—O—, being $R_4$ a radical selected from the group consisting of: phenyl, tolyl, mesitylenyl, naphthyl, bipheynylyl, quinolinyl N-oxide, quinolinyl N-sulfide and anthracenyl; and the other Z diradical is —O—$(C_1$-$C_6)$alkyl-O—, being the alkyl radical selected from methylene, ethylene, propylene, and butylene. In another embodiment of the compound (Ib), one of $Z_1$ and $Z_3$ is —O—P(=O)(Ph)-O—; and the other Z diradical is —O—$(C_1$-$C_6)$alkyl-O—, being the alkyl radical selected from methylene, ethylene, propylene, and butylene. In another embodiment of the compound (Ib), one of $Z_1$ and $Z_3$ is —O—P(=O)($R_4$)—O—, being $R_4$ a radical selected from the group consisting of: phenyl, tolyl, mesitylenyl, naphthyl, bipheynylyl, quinolinyl N-oxide, quinolinyl N-sulfide and anthracenyl; and the other Z diradical is —O—$CH_2$—O—. In another embodiment of the compound of formula (Ib) one of $Z_1$ and $Z_3$ is —O—P(=O)(Ph)-O— and the other Z diradical is —O—$CH_2$—O—. In another embodiment of the compound of formula (Ib), one of $Z_1$ and $Z_3$ is —O—$(C_1$-$C_6)$alkyl-O— and the other is —P(=O)(N$R_6$$R_7$)—, wherein $R_6$ and $R_7$ are as defined above. In another embodiment of the compound of formula (Ib), one of $Z_1$ and $Z_3$ is —O—$CH_2$—O— and the other is —P(=O)(N$R_6$$R_7$)—, wherein $R_6$ and $R_7$ are as defined above. In another embodiment of the compound of formula (Ib), one of $Z_1$ and $Z_3$ is —O—$CH_2$—O— and the other is —P(=O)(N$R_6$$R_7$)—, wherein $R_6$ and $R_7$ are the same. In another embodiment of the compound of formula (Ib), one of $Z_1$ and $Z_3$ is —O—$CH_2$—O— and the other is —P(=O)(N$R_6$$R_7$)—, wherein $R_6$ and $R_7$ are the same and are hydrogen. In another embodiment of the compound of formula (Ib), $Y_1$ to $Y_4$ are the same and are selected from the group consisting of: $(C_6$-$C_{20})$aryl; and $(C_6$-$C_{20})$aryl substituted with one or more radicals independently selected from the group consisting of: $(C_1$-$C_{20})$alkyl, $(C_1$-$C_6)$alkyl-O—, $(C_1$-$C_6)$haloalkyl, halogen, cyano, and nitro. In another embodiment of the compound of formula (Ib), $Y_1$ to $Y_4$ are $(C_6$-$C_{20})$aryl. In another embodiment of the compound of formula (Ib), $Y_1$ to $Y_4$ are phenyl. In another embodiment of the compound of formula (Ib), $R_2$ and $R_2'$ are hydrogen. In another embodiment of the compound of formula (Ib), $R_1$ is selected from methyl, ethyl, propyl, and butyl. In another embodiment of the compound of formula (Ib), $R_1$ is methyl. In another embodiment, $A_1$ and $A_2$ are —O— diradicals; G is —P(=O)($R_4$)—, or $(C_1$-$C_6)$alkyl; $R_4$ is a $(C_6$-$C_{20})$aryl radical; $Y_1$ to $Y_4$ are the same and are $(C_6$-$C_{20})$aryl; $FG_1$ and $FG_2$ are —OH and are in meta position; $R_2$ and $R_2'$ are hydrogen; and $R_1$ is $(C_1$-$C_{20})$alkyl. In another embodiment, the compound of formula (Ib) is selected from the compounds of formula (Ib1), (Ib2), (Ib3), (Ib4), (Ib5), (Ib10) and a stereoisomer thereof. In another embodiment, the compound of formula (Ib) is selected from the compounds of formula (Ib1), (Ib7), (Ib8), (Ib9), (Ib10), (Ib11), (Ib12), (Ib13) and a stereoisomer thereof. In another embodiment, the compound of formula (Ib) is selected from the compounds of formula (Ib1), (Ib7), (Ib8), (Ib9), (Ib10) and a stereoisomer thereof. In another embodiment, the compound of formula (Ib) is selected from the compounds of formula (Ib1), (Ib2), (Ib3), (Ib4), (Ib5), (Ib6), (Ib7), (Ib8), (Ib9), (Ib10) and a stereoisomer thereof. In another embodiment of the compound of formula (Ib), $R_1$ is methyl. In another embodiment, $A_1$ and $A_2$ are —O— diradicals; G is —P(=S)($R_5$)—; $R_5$ is a $(C_6$-$C_{20})$aryl radical; $Y_1$ to $Y_4$ are the same and are $(C_6$-$C_{20})$aryl; $FG_1$ and $FG_2$ are —OH and are in meta position; $R_2$ and $R_2'$ are hydrogen; and $R_1$ is $(C_1$-$C_{20})$alkyl. In another embodiment, the compound of formula (Ib) is one selected from the compounds of formula (Ib11), (Ib12), (Ib13), and a stereoisomer thereof.

In another embodiment, the compound of formula (Ib) is selected from a compound of formula (Ib1), (Ib2), (Ib7), (Ib8), (Ib9), (Ib10), (Ib11), (Ib12), (Ib13), and a stereoisomer thereof.

In another embodiment, the compound is one of formula (Ic). In another embodiment of the compound of formula (Ic) $Z_1$ to $Z_4$ are diradicals independently selected from the group consisting of: —O—P(=O)($R_4$)—O—, —N($R_3$)—P(=O)($R_4$)—N($R_3$)—, —N($R_3$)—P(=O)($R_4$)—O—, —O—P(=S)($R_5$)—O—, —N($R_3$)—P(=S)($R_5$)—N($R_3$)—, —N($R_3$)—P(=S)($R_5$)—O—, —N($R_3$)—S(=O)$_2$—N($R_3$)—, —N($R_3$)—S(=O)$_2$—O—, —O—S(=O)$_2$—O—, —O—$(C_1$-$C_6)$alkyl-O—, —O—$(C_1$-$C_6)$alkyl-N($R_3$)—, —N($R_3$)—$(C_1$-$C_6)$alkyl-N($R_3$), wherein $R_5$ is a radical selected from the group consisting of: phenyl, tolyl, mesitylenyl, naphthyl, bipheynylyl, quinolinyl N-oxide, quinolinyl N-sulfide and anthracenyl, wherein $R_3$, and $R_4$ are as defined above. In another embodiment of the compound of formula (Ic), $Z_1$ to $Z_4$ are the same. In another embodiment of the compound of formula (Ic), $Z_1$ to $Z_4$ are —O—P(=O)($R_4$)—O—, being $R_4$ as defined above. In another embodiment of the compound of formula (Ic), $Z_1$ to $Z_4$ are —O—P(=O)($R_4$)—O—, being $R_4$ a $(C_6$-$C_{20})$ aryl radical. In another embodiment of the compound of formula (Ic), $Z_1$ to $Z_4$ are —O—P(=O)($R_4$)—O—, being $R_4$ a phenyl radical. In another embodiment of the compound of formula (Ic), at least one of $Z_1$ to $Z_4$ is different from the others. In another embodiment of the compound of formula (Ic), $Z_2$, $Z_3$, and $Z_4$ are the same. In another embodiment of the compound of formula (Ic), one of $Z_1$ to $Z_4$ is —O—P(=O)($R_4$)—O—, wherein $R_4$ is as defined above, and the other three Z diradicals are the same and are selected from the group consisting of: —N($R_3$)—P(=O)($R_4$)—N($R_3$)—, —N($R_3$)—P(=O)($R_4$)—O—, —O—P(=S)($R_5$)—O—, —N($R_3$)—P(=S)($R_5$)—N($R_3$)—, —N($R_3$)—P(=S)($R_5$)—O—, —N($R_3$)—S(=O)$_2$—N($R_3$)—, —N($R_3$)—S(=O)$_2$—O—, —O—S(=O)$_2$—O—, —O—$(C_1$-$C_6)$alkyl-O—, —O—$(C_1$-$C_6)$alkyl-N($R_3$)—, —N($R_3$)—$(C_1$-$C_6)$alkyl-N($R_3$)—, wherein $R_3$, $R_4$, and $R_5$ are as defined above. In another embodiment of the compound of formula (Ic), one of $Z_1$ to $Z_4$ is —O—P(=O)($R_4$)—O—, and the other three Z diradicals are —O—$(C_1$-$C_6)$alkyl-O—. In another embodiment of the compound of formula (Ic), one of $Z_1$ to $Z_4$ is —O—P(=O)($R_4$)—O—, being $R_4$ $(C_6$-$C_{20})$aryl or $(C_6$-$C_{20})$aryl substituted as defined above, and the other three Z diradicals are —O—$(C_1$-$C_6)$alkyl-O—. In another embodiment of the compound of formula (Ic), one of $Z_1$ to $Z_4$ is —O—P(=O)($R_4$)—O—, the other Z diradicals are —O—$(C_1$-$C_6)$alkyl-O—, and $R_4$ is a $(C_6$-$C_{20})$aryl radical. In another embodiment of the compound (Ic), one of $Z_1$ to $Z_4$ is —O—P(=O)($R_4$)—O—, the other Z diradicals are —O—$(C_1$-$C_6)$alkyl-O—, and $R_4$ is selected from the group consisting of: phenyl, tolyl, mesitylenyl, naphthyl, bipheynylyl, quinolinyl N-oxide, quinolinyl N-sulfide and anthracenyl. In another embodiment of the compound (Ic), one of $Z_1$ to $Z_4$ is —O—P(=O)($R_4$)—O—, the other Z diradicals are —O—$(C_1$-$C_6)$alkyl-O—, and $R_4$ is a phenyl radical. In another embodiment of the compound of formula (Ic), one of $Z_1$ to $Z_4$ is —O—P(=O)(Ph)-O— and the other three Z diradicals are —O—$CH_2$—O—. In another embodiment of the compound of formula (Ic), $Y_1$ to $Y_4$ are the same. In another embodiment of the compound of formula (Ic) $Y_1$ to $Y_4$ are the same and are selected from the group consisting of: $(C_6$-$C_{20})$aryl; and $(C_6$-$C_{20})$aryl substituted with one or more radicals independently selected from the group consisting of: $(C_1$-$C_{20})$alkyl, $(C_1$-$C_6)$alkyl-O—, $(C_1$-$C_6)$haloalkyl, halogen, cyano, and nitro. In another embodiment of the compound of formula (Ic), $Y_1$ to $Y_4$ are $(C_6$-$C_{20})$aryl radicals as defined above. In another embodiment of the compound of formula (Ic), $Y_1$ to $Y_4$ are phenyl radicals. In another embodiment of the compound of formula (IC), $R_2$ and $R_2'$ are hydrogen. In another embodiment of the compound of formula (Ic), $R_1$ is $(C_1$-$C_{20})$alkyl. In another embodiment of the compound of formula (Ic), $R_1$ is selected from methyl, ethyl, propyl, dodecanyl, and isobutyl. In another embodiment of the compound of formula (Ic), $R_1$ is methyl. In another embodiment of the compound of formula (Ic), $R_1$ is dodecanyl. In another embodiment of the compound of formula (Ic), $R_1$ is $(C_3$-$C_{20})$alkenyl. In another embodiment of the compound of formula (Ic), $R_1$ is dodecenyl. In another embodiment, the compound of formula (Ic) is selected from (Ic1), (Ic2), (Ic3), (Ic4), and a stereoisomer thereof. In still yet another embodiment, the compound of formula (Ic) corresponds to the compound of formula (Ic1), (Ic3), (Ic4) or a stereoisomer thereof. In another embodiment, the compound of formula (Ic) is selected from (Ic1), and (Ic2). In another embodiment, the compound of formula (Ic) is selected from (Ic3), and (Ic4).

In another aspect, the present invention provides a process for the preparation of the compound of the present invention, as defined above.

In one embodiment, when the compound is one of formula (Ia), the process of the present invention comprises the reaction between a compound of formula (VIIA):

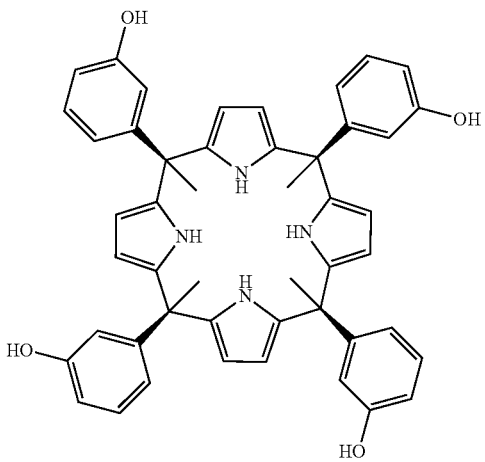

(VIIa)

and a compound of formula (VIII) as defined above.

In another embodiment, when the compound is one of formula (Ia), the process comprises the reaction between the compound of formula (VII) and a compound of formula (VIII), wherein G is selected from —P(=O)NR$_6$R$_7$—, —P(=O)(R$_4$)—, —S(=O)$_2$—, and —(C$_1$-C$_6$)alkyl-, B$_1$ and B$_2$ are halogen, and R$_4$ is as defined in any of the previous embodiments. In another embodiment, when the compound is one of formula (Ia1) or (Ia3), the process comprises the reaction between the compound of formula (VIIA) and a compound of formula (VIII), wherein G is —P(=O)(R$_4$)—, B$_1$ and B$_2$ are halogen, and R$_4$ is (C$_6$-C$_{20}$) aryl. In another embodiment, when the compound is one of formula (Ia1) or (Ia3), the process comprises the reaction between the compound of formula (VIIA) and a compound of formula (VIII), wherein G is —P(=O)(R$_4$)—, B$_1$ and B$_2$ are halogen, and R$_4$ is phenyl. In another embodiment, when the compound is one of formula (Ia2), the process comprises the reaction between the compound of formula (VIIA) and a compound of formula (VIII), wherein G is methyl, and B$_1$ and B$_2$ are halogen. In another embodiment, the compound of formula (VIII) is selected from phenylphosphonic dichloride and bromochloromethane.

In another embodiment, when the compound is one of formula (Ib), the process of the present invention comprises the reaction between a compound of formula (VIIA) and a compound of formula (VIII), as defined above. In another embodiment, when the compound is one of formula (Ib), the process comprises the reaction between the compound of formula (VII) and a compound of formula (VIII), wherein G is selected from —P(=S)(R$_5$)—, —P(=O)(R$_4$)— and —(C$_1$-C$_6$)alkyl-, B$_1$ and B$_2$ are halogen, and R$_4$ and R$_5$ are as defined in any of the previous embodiments. In another embodiment, when the compound is one of formula (Ib1) or (Ib2), the process comprises the reaction between the compound of formula (VIIA) and a compound of formula (VIII), wherein G is selected from —P(=O)(R$_4$)— and —(C$_1$-C$_6$)alkyl-, B$_1$ and B$_2$ are halogen, and R$_4$ is as defined in any of the previous embodiments. In another embodiment, when the compound is one of formula (Ib1) or (Ib2), the process comprises the reaction between the compound of formula (VIIA) and a compound of formula (VIII), wherein G is —P(=O)(R$_4$)—, B$_1$ and B$_2$ are halogen, and R$_4$ is (C$_6$-C$_{20}$) aryl. In another embodiment, when the compound is one of formula (Ib1) or (Ib2), the process comprises the reaction between the compound of formula (VIIA) and a compound of formula (VIII), wherein G is —P(=O)(R$_4$)—, B$_1$ and B$_2$ are halogen, and R$_4$ is phenyl. In another embodiment, when the compound is one of formula (Ib1) or (Ib2), the process comprises the reaction between the compound of formula (VIIA) and a compound of formula (VIII), wherein G is methyl, and B$_1$ and B$_2$ are halogen. In another embodiment, the compound of formula (VIII) is selected from phenylphosphonic dichloride and bromochloromethane.

In another embodiment, when the compound is one of formula (Ib7), (Ib8) or (Ib9), the process comprises the reaction between the compound of formula (VIIA) and a compound of formula (VIII), wherein G is selected from —P(=O)(R$_4$)— and —(C$_1$-C$_6$)alkyl-, B$_1$ and B$_2$ are halogen, and R$_4$ is as defined in any of the previous embodiments. In another embodiment, when the compound is one of formula (Ib7), (Ib8) or (Ib9), the process comprises the reaction between the compound of formula (VIIA) and a compound of formula (VIII), wherein G is —P(=O)(R$_4$)—, B$_1$ and B$_2$ are halogen, and R$_4$ is (C$_6$-C$_{20}$)aryl.

In another embodiment, when the compound is one of formula (Ib7), (Ib8) or (Ib9), the process comprises the reaction between the compound of formula (VIIA) and a compound of formula (VIII), wherein G is —P(=O)(R$_4$)—, B$_1$ and B$_2$ are halogen, and R$_4$ is phenyl. In another embodiment, the compound of formula (VIII) is phenylphosphonic dichloride.

In another embodiment, the compound of formula (Ib11), (Ib12) or (Ib13) can be obtained by a process comprising:
(i) the reaction between a compound of formula (VIIA) with phenylphosphine dichloride; and
(ii) mixing the product of step (i) with sulphur (S$_2$).

In another embodiment, the compound of formula (Ib1) or (Ib2) can be obtained by a process comprising the reaction between a compound of formula (Ia1) or (Ia3) as defined above, and a compound of formula (VIII) wherein G is —(C$_1$-C$_6$)alkyl-, and B$_1$ and B$_2$ are halogen.

In another embodiment, the compound (Ib6) can be obtained reacting the compound of formula (Ia6) as defined above with a compound of formula (IX):

Cl—P(X)Ar-Cl                     (IX)

wherein X means O or S; and Ar means tolyl, mesitylenyl, naphthyl, quinolinyl N-oxide, quinolynyl N-sulfide, bipheynylyl, and anthracenyl.

In another embodiment, when the compound is one of formula (Ic1), (Ic3) or (Ic4), the process of the present invention comprises the reaction between a compound of formula (VIIb) wherein $R_1$ is methyl or dodecanyl:

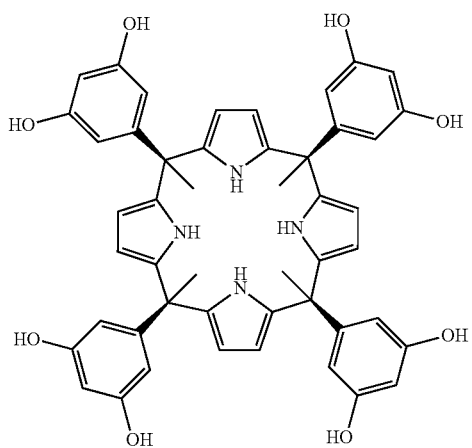

(VIIb)

with a compound of formula (VIII) as defined above. In another embodiment, when the compound is one of formula (Ic1), the process comprises the reaction between the compound of formula (VIIb) and a compound of formula (VIII), wherein G is —P(=O)($R_4$)—, $B_1$ and $B_2$ are halogen, and $R_4$ is as defined in any of the previous embodiments. In another embodiment, when the compound is one of formula (Ic1), (Ic3) or (Ic4), the process comprises the reaction between the compound of formula (VIIb) wherein $R_1$ is methyl or dodecanyl and a compound of formula (VIII), wherein G is selected from —P(=O)($R_4$)—, $B_1$ and $B_2$ are halogen, and $R_4$ is ($C_6$-$C_{20}$)aryl. In another embodiment, when the compound is one of formula (Ic1), (Ic3) or (Ic4), the process comprises the reaction between the compound of formula (VIIb) wherein $R_1$ is methyl or dodecanyl and a compound of formula (VIII), wherein G is selected from —P(=O)($R_4$)—, $B_1$ and $B_2$ are halogen, and $R_4$ is phenyl.

In the process for preparing the compounds of formula (Ia), (Ib), or (Ic) the basic medium is selected from the group consisting of a tertiary amine—$NR_9R_{10}R_{11}$, being $R_9$, $R_{10}$, and $R_{11}$ radicals independently selected and representing ($C_1$-$C_6$)alkyl; pyridine; alkaline carbonate; and alkaline ($C_1$-$C_6$)alkyl-O—. Preferably, the basic medium is a tertiary amine or an alkaline carbonate. In an embodiment, the basic medium is selected from the group consisting of triethylamine and diisopropylethylamine. In another embodiment, the basic medium is potassium carbonate. The molar ratio between the basic medium required in the preparation of a compound of formula (Ia), (Ib), or (Ic) and the compound of formula (VIII) is comprised from 2:1 to 15:1.

The term "molar ratio" between two products refers to the relation of moles of one product vs. the moles of the other product. In the case of the molar ratio between the basic medium and the compound of formula (VIII), this means the relation of moles of basic medium vs. the moles of the compound of formula (VIII).

The term "weight ratio" between two products refers to the relation of weight of one product vs. the weight of the other product, both weights being expressed in the same units. In the case of the weight ratio between the plasticizer and the compound of the invention, this means the relation of weight of plasticizer vs the weight of compound of the invention, both expressed in mg.

In another aspect, the present invention provides a membrane comprising a compound selected from the compounds of formula (Ia), (Ib), (Ic), (IV), (V) and a stereoisomer thereof, or alternatively the compound is one of formula (VI), together with a plasticizer, a cation-exchanger salt, and a polymeric matrix.

The polymeric matrix comprises a polymer or mixture of polymers of high molecular average weight, typically comprised from 70000 to 250000. With such a molecular weight it is guaranteed the inert character of the polymer, independently of its chemical composition. In one embodiment, the polymer(s) composing the polymeric matrix has a molecular average weight comprised from 70000 to 250000. In another embodiment the polymer(s) has a molecular average weight comprised from 100000 to 200000. The polymer or mixture of polymers is able of forming thin films. Illustrative non-limitative examples of polymers are polyvinyl chloride (also carboxylated), poly(vinylidene chloride), polyvinyl chloride/polyvinyl alcohol, Urushi (Japanese lacquer) acrylate, polysiloxane, siloxane sol-gel and monolayer, poly(acrylonitrile), polyurethanes (particularly aromatic), poly(vinyl butyral), poly(vinyl formal), poly(vinyl acetate), silicone elastomers, cellulose esters and polycarbonates.

In one embodiment the polymeric matrix comprises a mixture of polymers of the same or different chemical nature. The skilled person, making use of the general knowledge, can routinely choose, among those available in the state of the art, the appropriate polymer(s) in the appropriate amount(s) depending on the compound selected as ionophore.

The term "same chemical nature", when comparing two or more polymers forming the polymeric matrix, has to be understood as polymers with the same functional groups in their backbones but differing in the molecular average weight. An illustrative non-limitative example of a mixture of polymers of the "same nature" would be a mixture of polyurethanes, wherein the common functional group to all polyurethanes is the urethane group.

The term "different chemical nature", when comparing two or more polymers forming the polymeric matrix, has to be understood as polymers with the different functional groups in their backbones. An illustrative non-limitative example of a mixture of polymers of "different chemical nature" would be a mixture of polyurethane (wherein the functional group is an urethane) and PVC (wherein the functional group is the vinyl chloride).

Advantageously, such a polymer, in combination with the plasticizer, facilitates ionic mobility across the membrane interface.

The person skilled in the art is able, making use of the general knowledge, of selecting those more appropriate polymers and adjusting the amounts, depending on the ionophore to be manufactured in the form of an ion-selective membrane (Bakker E. et al., 1997). In one embodiment, the % by weight of polymeric matrix is comprised from 20 to 40%. In another embodiment, the % by weight of polymeric matrix is comprised from 25 to 35%. In another embodiment, the % by weight of polymeric matrix is comprised from 28 to 32%.

The term "percentage (%) by weight" refers to the percentage of each component of the membrane in relation to the total weight of the membrane composition.

In one embodiment, the polymer is poly(vinyl chloride) (PVC). In another embodiment the PVC used has a molecular weight comprised from 70000 to 250000. In another embodiment the polymer is PVC having a molecular weight comprised from 100000 to 200000. In another embodiment, the PVC is in a % by weight comprised from 20 to 40%. In another embodiment, the % by weight of PVC is comprised from 25 to 35%. In another embodiment, the % by weight of PVC is comprised from 28 to 32%.

The term "plasticizer" has to be understood in the present invention as any of the available plasticizers for the manufacturing of ion-selective membranes. Typical plasticizers are for example (but not restricted to) 2-nitrophenyl octyl ether (o-NPOE), bis(2-ethylhexyl) sebacate (DOS) and chloroparaffin, as well as other chemical structures such as phthalates, adipates suberates, azelates, glutarates, succinates and hexahydrophtalates. Other non-polymeric discrete organic compounds having low molecular weight (usually of 500 to 20.000 molecular weight) and a boiling temperatures comprised from 150 to 500° C., can also be used as plasticizers. The function of the plasticizers is to make the membrane softer and much more resistant to mechanical stress such as poking, bending or stretching, as well as reducing the glass transition temperature and increasing the polarity of the membrane. Plasticizers also enhance the flexibility by facilitating the movement of the polymer macromolecules and thus influence the partitioning of ions. The plasticizer must be miscible with the polymeric matrix in the membrane in order to obtain a homogeneous dispersion. Typical mixtures of plasticizer with the polymeric matrix are in a weight ratio comprised from 1:1 to 4:1 (plasticizer:polymer). The plasticizer is present in the membrane in the amount sufficient to solvate the creatinine receptor, anywhere in a weight ratio vs the amount of ionophore comprised 10:1 to 100:1. In one embodiment the weight ratio between the plasticizer and the ionophore is comprised from 10:1 to 30:1. In one embodiment the weight ratio between the plasticizer and the ionophore is comprised from 15:1 to 25:1. In another embodiment, the plasticizer is in a % by weight comprised from 40 to 80%. In another embodiment, the plasticizer is in a % by weight comprised from 55 to 65%. In one embodiment, the plasticizer is 2-nitrophenyl octyl ether. In another embodiment, the weight ratio plasticizer:polymeric matrix is comprised from 1:1 to 4:1. In another embodiment, the weight ratio plasticizer:polymeric matrix is comprised from 2:1 to 3:1. In another embodiment the plasticizer is 2-nitrophenyl octyl ether, and the weight ratio between the 2-nitrophenyl octyl ether and the polymeric matrix is comprised from 2:1 to 3:1. In another embodiment the plasticizer is 2-nitrophenyl octyl ether, it is in % by weight comprised from 55 to 65%, and the weight ratio between the 2-nitrophenyl octyl ether and the polymeric matrix is comprised from 2:1 to 3:1.

The membrane of the sensor also includes a cation-exchanger salt which is also soluble in the polymeric matrix. This salt is typically composed, on one hand, by a large organic molecule which is an anion (negatively charged). On the other hand, the counterion is a small cation, such as alkali metals, among many other possibilities. The role of this salt is to facilitate the entrapment of the target analyte from the ionophore in case it is a neutral macromolecule. The inclusion of this lipophilic ionic salt helps to maintain the permselectivity of the membrane where each cation is complemented by a lipophilic anion from the ion-exchanger. The cation exchanger avoids coextraction of ions with different charges from the sample into the membrane phase in order to accomplish the theoretical Nernstian behavior from an ion-selective electrode. The presence of cation exchanger is required to obtain a membrane that exchanges ions with the same charge sign (called permselectivity or Donnan exclusion). Illustrative non-limitative examples of cation-exchanger salts useful in the manufacture of ion-selective membranes are: sodium tetrakis-[3,5-bis(1,1,1,3,3,3-hexafluoro-2-methoxy-2-propyl)-phenyl]borate trihydrate (NaHFPB) and potassium tetrakis[3,5-(trifluoromethyl)phenyl]borate (KTFPB).

In one embodiment, the molar ratio of the compound of formula (Ia), (Ib), (Ic), (IV), (V), or a stereoisomer thereof, or alternatively of a compound of formula (VI) and the ion-exchanger salt is comprised from 10:1 to 10:4. This range of molar ratio guarantees the selectivity of the ionophore for its specific analyte (creatinine) to other species present in real samples. The final molar ratio will depend on the particular ion-exchanger salt and ionophore. As it is illustrated below, when the cation-exchanger salt is KTFPB and the ionophore is the compound (Ib1), the optimal molar ratio was about 10:3. It was found that with such a ratio the best results for the sensor were obtained, leading to complement the creatinine positive charge in the ion-selective membrane by first excluding the $K^+$ from the cation-exchanger salt in the membrane with creatinine from the sample.

In another embodiment, the amount in % by weight of ion-exchanger salt is comprised from 0.1 to 2%. In another embodiment, the amount is about 1%.

The creatinine-selective membrane of the invention is prepared by dissolving all components in a suitable organic solvent, such as tetrahydrofuran. This solution containing all the membrane components dissolved can be referred hereinafter as "membrane cocktail" and it is used to form the membrane by suitable evaporation of the solvent.

The membrane composition may also include chemical substances, nanomaterials or any type of compound that act as "ion-to-electron" transducer, facilitating the generation and stability of the potentiometric signal, as described in the literature. The need to incorporate these substances, and the way to do it, will be evident for any person with knowledge in the field (Tanji yin and Wei qin, 2013).

As the skilled person will recognize, when preparing a membrane composition of the invention, the different components will be in such amounts that they sum up 100% by weight.

The membrane described here can be used to build electrodes with different configurations. Electrodes for the determination of the content of a liquid sample have been described by others. They commonly contain a plastic membrane which has an ion-selective component (ionophore) and a solvent/plasticizer compound in which the ion-selective component can be dissolved. In addition to glasses selectively permeable to ions, hydrogen ionophores such as lipophilic derivatives of uncouplers of oxidative phosphorylation and lipophilic tertiary amines have been used.

The two most common arrangements are solid-contact ISE and the inner solution ISE. There are different ways to build these ISE. Some typical examples are given below.

a) Solid-Contact Ion-Selective Electrode (Solid Contact ISE)

Transducer Layer

A transducer element is required in order to avoid the formation of capacitive layers that affect the stability of the potentiometric readings. Illustrative non-limitative examples of these transducing components are electroactive conjugated polymers (conducting polymers), as well as a variety of nanomaterials, such as three-dimensionally ordered mesoporous (3DOM) carbon and different types of carbon nanotubes (CNTs).

Ion-Selective Membrane

A solid contact potentiometric sensor is obtained by casting a suitable volume of the polymeric membrane cocktail onto a conductive substrate which can be a transducer layer previously deposited, or alternatively, incorporated into the membrane cocktail. Next, the solvent is evaporated, in order to form a suitable membrane. Alternatively, the solid transducer element can be incorporated with the ion-selective membrane cocktail. Other methods of membrane deposition include dip coating, where the substrate with the transducing layer is submerged into the ion-selective membrane cocktail; spin coating, where the conductor is spun and immersed into the ion-selective membrane cocktail and removed to let it dry.

Once the membrane is fully dried onto the conductor, the electrode is submerged into a conditioning solution until stable readings of potential are obtained.

b) Inner-Solution Ion-Selective Electrode (Inner Solution ISE)

In the case of ion-selective electrode with inner filling solution, the polymeric membrane is cast onto a glass-casting plate. Once dried, the membrane is gently peeled off and placed in the membrane packing piece of the electrode and finally pressed with the membrane housing to put the membrane in contact with the inner electrolyte solution, which is 10 mM of creatinine in 10 mM buffer solution, the buffer solution providing a pH which is below the creatinine pKa value. Finally, the polymeric membrane is placed in contact with a conditioning solution until stable potential readings are obtained.

The buffer for conditioning can be any able to control the pH at values in the range from approximately 3 to approximately 4.5. Buffer solutions can be (but are not restricted to) acetic acid/acetate, phosphate/citrate, etc., adjusted to the suitable pH value.

The conditioning of the creatinine membrane once completely dried consists of immersing the membrane in a buffer solution for such a period of time that allows obtaining stable potential readings along with a creatinine concentration equal or higher than 1 mM. As the skilled in the art will recognize, when working at lower concentrations the time required to condition the electrode will be higher than the one required using higher concentrations.

The calibration of the electrode is carried out with a buffer solution whose concentration is equal or higher than 10 mM with increasing concentration of creatinine by adding known amounts of creatinine standards. The maximum concentration raised could be about 0.1 M.

In another aspect the present invention provides a device comprising the electrode of the invention.

In one embodiment, the device (or potentiometric cell) consists of two electrodes: a reference electrode that keeps a stable and constant potential during the measurements, and the working electrode, in this case the ion-selective electrode, which in this case includes the creatinine selective membrane. The reference electrode can be any type of commercial or home-made system, such as (but not restricted to) silver-silver chloride electrode (in its multiple forms), calomel electrode, etc., that keeps a stable and constant potential during the measurements. In one embodiment, the reference electrode is a silver-silver chloride electrode. The working electrode can be either the inner solution ISE or the solid contact ISE, or any other configurations containing the polymeric membrane described above. In one embodiment, the reference electrode is a double junction Ag/AgCl/KCl 3 M reference electrode containing 1 M LiAcO as electrolyte bridge, type 6.0729.100 (Metrohm AG, Switzerland).

The measuring circuit is assembled in order to be able to properly record the electromotive force generated between these electrodes by a voltmeter. Other measurement arrangements using other electrochemical approaches, such as for example chronopotentiometry, pulsetrodes, cyclic voltammetry, etc. or any other techniques using these membranes are also possible. This membrane can also be used for building alternative potentiometric methods, such as those using field effect transistors (ISFET)

There are other potentiometric platforms which can be implemented with this creatinine membrane. A few examples of wearable and disposable sensors to detect creatinine have already been reported, although none of them offered reliable results. One of these possible platforms is onto screen-printed electrodes (SPE) or inkjet-printed electrodes (IPE), which provides a way to reduce the size of the potentiometric cell as well as a way to make them disposable. SPE and IPE have been widely used as potentiometric sensors. Other examples recently introduced that reduce massively the cost of this sensor are (but not restricted to) textiles, papers, rubbers, bandages, carbon fibers, and are possible, as far as the working sensing part of these devices is made by depositing the creatinine membrane by dip-coating, drop-casting, drip-coating, spin-coating, or any other suitable approach to cast a membrane. Embedded sensors, such as those recently described using temporary epidermal printing (tattoos), are also possible.

In another aspect, the present invention provides a process for quantifying the creatinine in a test sample.

The test sample can be any bodily test sample, such as blood, urine, and serum, among others.

The correlation step between the potential value measured and the concentration of creatinine can be performed generating previously a calibration curve. It is well-known for the skilled person in the art how to obtain such a pattern curves. Briefly, solutions of known creatinine concentration are prepared and the potential reading is performed with the electrode of the invention for each one of the solutions. With those readings, it is possible to generate a curve with the correlation between the concentration of creatinine and potential value. From that, measuring the potential in a test sample, this potential reading is applied in the calibration curve and a creatinine concentration value is obtained. The statistical treatment of the data can be performed using different well-known approaches.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

Unless otherwise stated, all the reagents were obtained from Sigma-Aldrich and were used without further purification unless otherwise stated. All solvents were commercially obtained and used without further purification with the exception of THF which was dried and deoxygenated using an MBraun SPS-800 solvent purification system. Routine 1H NMR spectra were recorded on a Bruker Avance 300 (300 MHz for 1H NMR), Bruker Avance 400 (400 MHz for 1H NMR) or a Bruker Avance 500 (500 MHz for 1H NMR) ultrashield spectrometer. The deuterated solvents (Aldrich) used are indicated in the experimental part; chemical shifts are given in ppm. For CDCl$_3$ the peaks were referenced relative to the solvent residual peak $\delta$H=7.26. For D6-acetone the peaks were referenced relative to the solvent residual peak $\delta$H=2.05 ppm. For D4-methanol the peaks were referenced relative to the solvent residual peak $\delta$H=3.31 ppm. All NMR J values are given in Hz and are uncorrected. Flash column chromatography was performed with Silica gel Scharlab60.

Example 1: Synthesis of Starting Tetrahydroxy Calixpyrrole (VIIA)

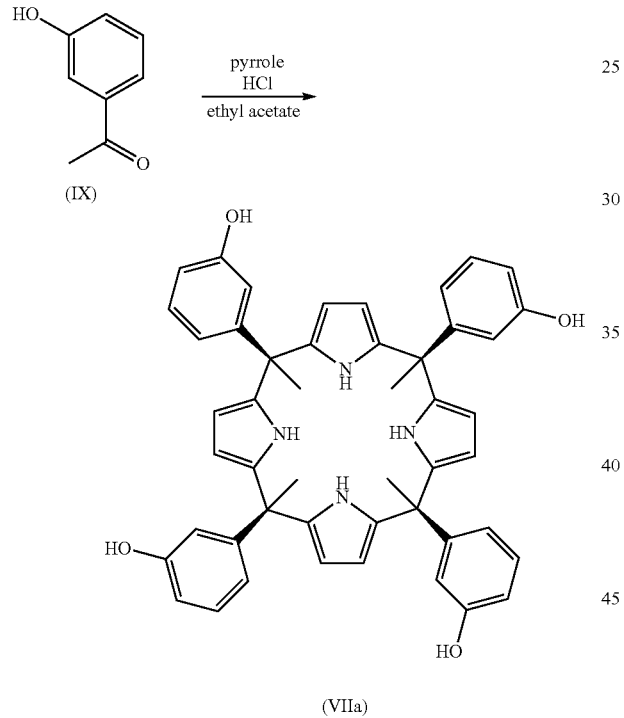

(VIIa)

Concentrated HCl(aq) (36% by weight, 25.3 mL, 0.3 mol, 10 equiv.) followed by pyrrole (2.2 mL, 31 mmol, 1.05 equiv.) were added to a solution of 1-(3-hydroxyphenyl) ethanone (4.04 g, 1 equiv.) in ethylacetate (300 mL, 0.1 M) under air. The resultant mixture was stirred for 14 hours at room temperature (RT) under air. The reaction mixture was neutralized with saturated NaHCO$_3$(aq) and extracted with CH$_2$Cl$_2$ (3×100 mL). The organic extracts were combined, dried over Na$_2$SO$_4$ and concentrated under vacuum to give a pale brown powder. This powder was purified by column chromatography (silica gel, 1% MeOH in CH$_2$Cl$_2$ to 10% MeOH in CH$_2$Cl$_2$, Rf of product was 0.25 with 5% MeOH in CH$_2$Cl$_2$ eluent). The fractions containing principally the desired product were collected together and evaporated under vacuum to give a white powder. This material was recrystallized from boiling MeCN (200 mL) to give pure product as small colourless cubes, 1.925 g (35% yield).

Starting Tetrahydroxy Calixpyrrole

1H NMR (400 MHz, D6-acetone, 25° C.) $\delta$ (ppm) 1.83 (s, 12H), 1.88 (s, 6H), 5.33 (d, J=8.2, 1H), 5.99-6.06 (m, 8H), 6.34-6.40 (m, 3H), 6.42 (ddd, J=7.8, 1.8, 1.0, 2H), 6.55 (ddd, J=8.1, 2.5, 1.0, 2H), 6.64-6.73 (m, 4H), 6.80 (dd, J=2.5, 1.6, 2H), 7.04 (t, J=7.9, 2H), 7.07 (t, J=7.9, 2H), 8.18 (s, 2H), 8.53 (1H), 8.73 (1H), 8.77 (s, 2H).

Example 2: Synthesis of Starting Octahydroxy Calixpyrrole (VIIb)

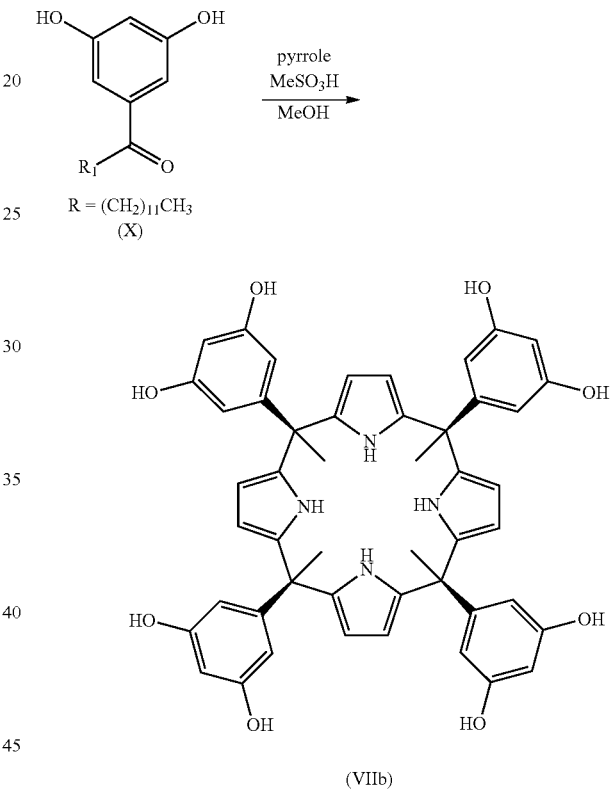

(VIIb)

Methanesulfonic acid (0.24 mL, 10.77 mmol, 3 equiv.) was added dropwise to a solution of pyrrole (0.25 mL, 3.6 mmol, 1 equiv.) in MeOH (6 mL). The mixture was stirred for 5 min and then a solution of dodecyl-(3',5')dihydroxyphenyl ketone (X) (1.1 g, 3.6 mmol, 1 equiv.) in MeOH (18 mL) was added slowly. The reaction was stirred 20 h at RT. The reaction mixture was diluted with water (30 mL) and extracted with ethyl acetate (4×50 mL). The organic layers were combined, dried over sodium sulphate, and concentrated under vacuum. The material was purified by chromatography (silica gel; dichloromethane/ethyl acetate-8:2→6:4) affording a brownish solid that was recrystallized from acetonitrile to give the pure product, 245 mg (19% yield).

Starting Octahydroxy Calixpyrrole (VIIb)

1H NMR (500 MHz, MEOD, 25° C.): $\delta$ 8.89 (bs, 4H), 6.18 (d, J=2.0, 8H), 6.15 (t, J=2.0, 4H), 5.89 (d, J=2.4, 8H), 2.30 (m, 8H), 1.35 (m, 80H), 0.89 (t, J=7.0, 12H).

Example 3: Synthesis of Single Carbon-Bridge Calixpyrrole (Type I)

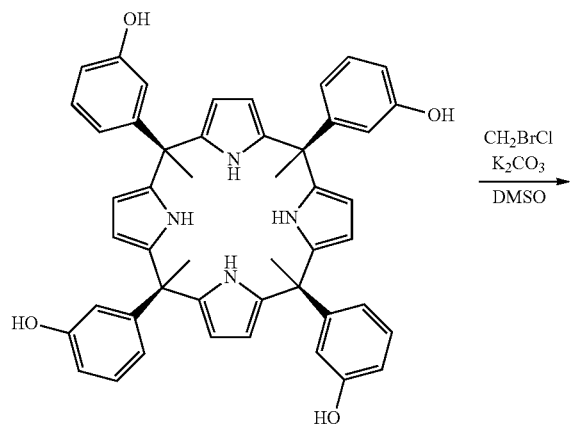

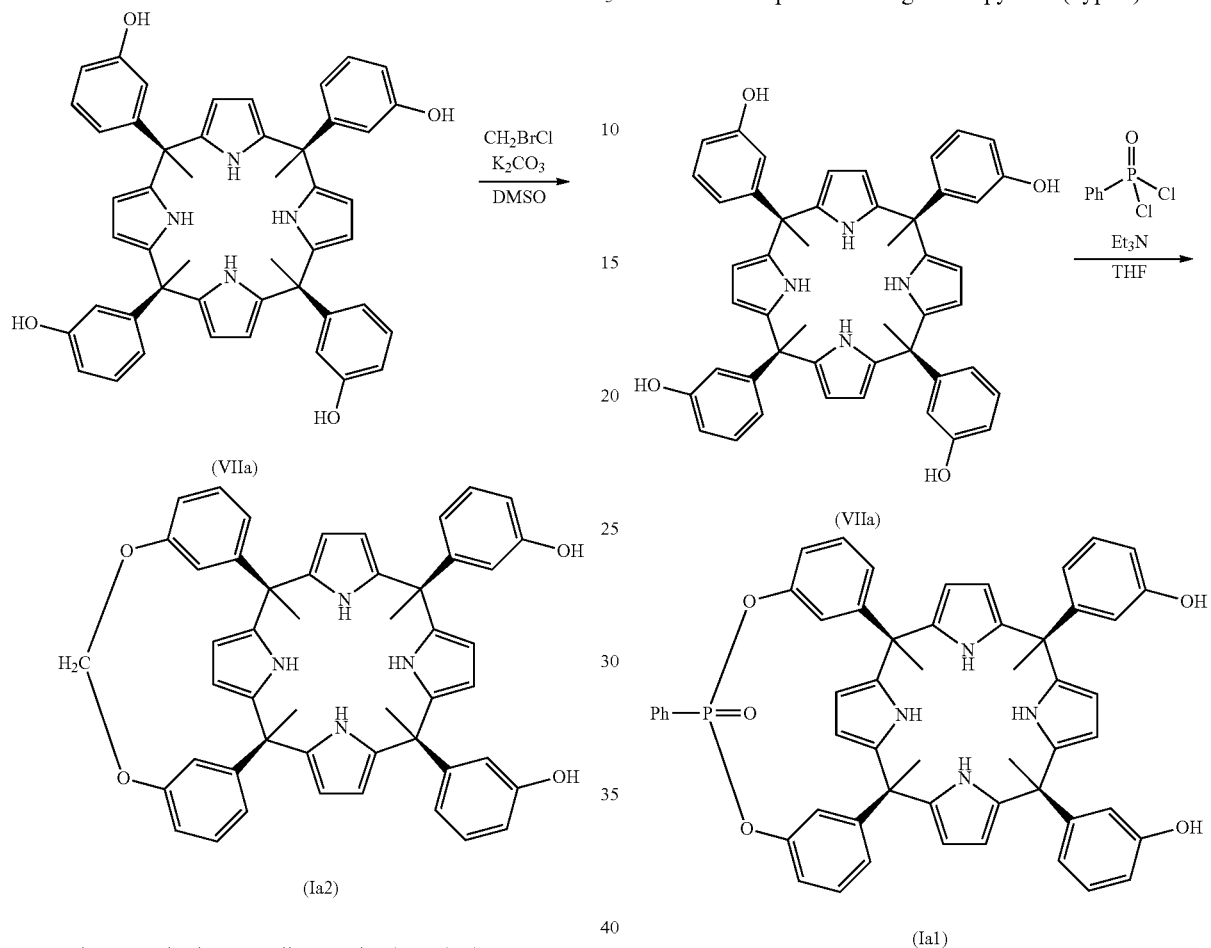

Starting tetrahydroxy calixpyrrole (VIIA) (41 mg, 55 μmol, 1 equiv.) and K₂CO₃ (16 mg, 112 μmol, 2 molar equiv.) were added to a sealable tube. This tube was placed under vacuum for 10 hours to remove as much water as possible from the reagents. The sealed tube was purged with Argon three times. Dimethyl sulfoxide (DMSO) (5.3 mL, 10 mM) was added followed by bromochloromethane (3.6 μL, 55 μmol, 1 equiv.) and the tube was sealed. The turbid reaction mixture was placed in an oil bath set to 100° C. and stirred for 1 hour. The reaction mixture was cooled, the sealed tube was opened and the mixture was brought to ≈pH 2 with 1M HCl(aq). The resultant mixture was extracted with CH₂Cl₂ (2×10 mL). The combined organic extracts were washed with water, dried over Na₂SO₄, and evaporated to give a light beige powder. This material was purified by column chromatography (silica gel, 1% MeOH in CH₂Cl₂ to 10% MeOH in CH₂Cl₂, Rf of product is 0.33 with 4% MeOH in CH₂Cl₂ eluent). Fractions containing the desired compound were collected together and evaporated under vacuum to give pure single carbon-bridge calixpyrrole as a white powder, 19 mg (44% yield).

Single Carbon-Bridge Calixpyrrole (Type I)

1H NMR (400 MHz, D6-acetone, 25° C.) δ (ppm) 1.99 (s, 6H), 2.00 (s, 6H), 5.68 (t, J=3.0 Hz, 2H), 5.77 (t, J=3.0 Hz, 2H), 6.13 (d, J=2.6 Hz, 2H), 6.18 (d, J=2.6 Hz, 2H), 6.76-6.80 (m, 2H), 6.90-6.97 (m, 4H), 7.00 (d, J=7.9 Hz, 2H), 7.07-7.15 (m, 6H), 7.22 (t, J=7.9, 2H), 7.49-7.69 (m, 6H), 7.83 (s, 1H), 7.95-8.03 (m, 4H), 8.07 (s, 2H), 8.48 (s, 1H).

Example 4: Synthesis of Single in-Phosphonate-Bridge Calixpyrrole (Type I)

Triethylamine (0.22 mL, 1.6 mmol, 2.2 equiv.) followed by phenylphosphonic dichloride (0.11 mL, 0.80 mmol, 1.1 equiv.) were added to a solution of starting tetrahydroxy calixpyrrole (VIIA) (536 mg, 0.72 mmol, 1 equiv.) in THF (anhydrous and degassed, 55 mL, 13 mM) stirring at RT under Argon atmosphere. The reaction mixture was stirred at RT for 16 hours during which time a white precipitate was formed in the reaction mixture. At this time the reaction mixture was brought to ≈pH 2 with 1M HCl(aq) and the resultant mixture was extracted with CH₂Cl₂ (3×100 mL). The organic extracts were combined, dried over Na₂SO₄ and evaporated under vacuum to give a white powder. This material was purified by column chromatography (silica gel, 1 MeOH in CH₂Cl₂ to 10% MeOH in CH₂Cl₂, Rf of the desired in-isomer is 0.40 with 5% MeOH in CH₂Cl₂ as eluent, Rf of the undesired out-isomer is 0.45 with 5% MeOH in CH₂Cl₂ as eluent). The fractions containing only the desired product were collected together and evaporated under vacuum to give pure material as a white powder. The fractions containing a mixture of the desired product and the undesired out-isomer were collected separately. These mixed fractions were concentrated under vacuum to give a white powder. This powder was dissolved as best as possible in boiling MeCN (10 mL). The hot mixture was passed through a simple paper filter into a round bottom flask. The filter was washed through with another portion of hot MeCN (5 mL). Over one night, as the solution cooled small colourless crystals of the desired product were formed. Total single in-phosphonate-bridge calixpyrrole collected=119 mg (19% yield).

Single In-Phosphonate-Bridge Calixpyrrole (Type I)

1H NMR (400 MHz, CDCl3, 25° C.) δ (ppm) 1.91 (s, 6H), 2.01 (s, 6H), 5.58 (d, J=2.6 Hz, 2H), 5.78 (t, J=3.0 Hz, 2H), 5.90 (d, J=3.1 Hz, 2H), 6.15 (d, J=2.6 Hz, 2H), 6.31 (s, 2H), 6.44 (t, J=2.1, 2H), 6.52 (dd, J=8.0, 2.4, 2H), 6.66 (d, J=8.1, 2H), 6.88, d, J=8.0, 2H), 6.91 (t, J=1.9, 2H), 6.99-7.05 (m, 4H), 7.20 (t, J=7.9, 2H), 7.57 (ddd, J=8.9, 7.1, 4.9, 2H), 7.64-7.70 (m, 1H), 7.92 (s, 1H), 7.99 (ddd, J=14.5, 8.3, 1.3, 2H), 8.23 (s, 2H), 8.62 (s, 1H).

Analogously to this process, the stereoisomer (Ia3) was obtained as a by-product of this reaction that can be separated from (Ia1) during the step of column chromatography under the conditions disclosed above.

Example 5: Synthesis of Di-Carbon-Bridged Calixpyrrole (Type Ib)

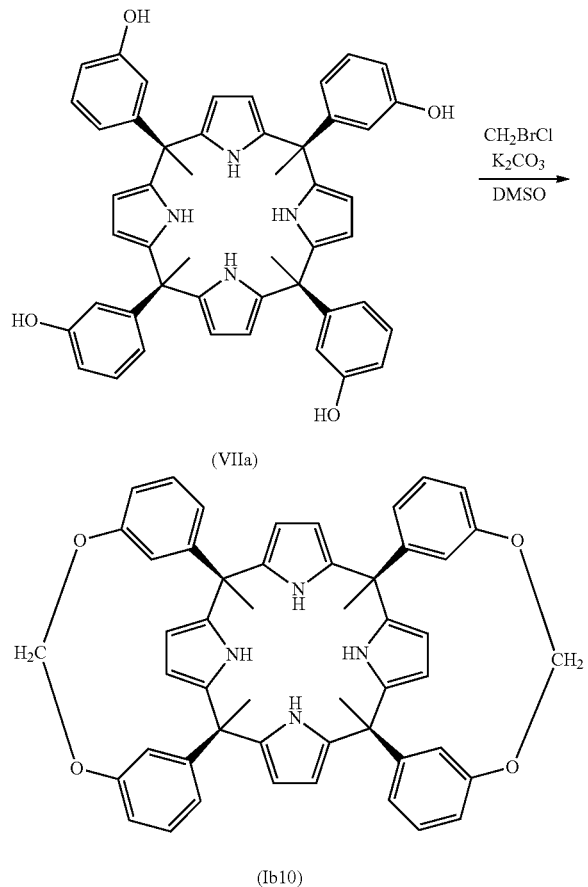

Starting tetrahydroxy calixpyrrole (VIIA) (40 mg, 54 μmol, 1 equiv.) and K$_2$O0$_3$ (60 mg, 432 μmol, 8 molar equiv.) were added to a sealable tube. This tube was placed under vacuum for 10 hours to remove as much water as possible from the reagents. The sealed tube was purged with Argon 3 times. DMSO (5.3 mL, 10 mM) was added followed by bromochloromethane (18 μL, 270 μmol, 5 equiv.) and the tube was sealed. The turbid reaction mixture was placed in an oil bath set to 100° C. and stirred for 1 hour. The reaction mixture was cooled, the sealed tube was opened and the mixture was brought to≈pH 2 with 1M HCl(aq). The resultant mixture was extracted with CH$_2$Cl$_2$ (2×10 mL). The combined organic extracts were washed with water, dried over Na$_2$SO$_4$, and the CH$_2$Cl$_2$ was evaporated to give a light beige powder. This material was suspended in MeCN (1 mL), the mixture was sonicated and the MeCN was decanted. The remaining solid was dried under vacuum to give the pure di-carbon-bridged receptor (Ib10) as a white powder, 32 mg (77% yield).

Di-Carbon-Bridged Calixpyrrole (Ib10)

1H NMR (300 MHz, CDCl3, 25° C.) δ (ppm) 1.85 (s, 12H), 5.34 (d, J=7.9, 2H), 6.04 (d, J=2.6 Hz, 4H), 6.07 (d, J=2.6 Hz, 4H), 6.17 (d, J=7.8, 2H), 6.61-6.69 (m, 8H), 6.71-6.76 (m, 4H), 6.97 (t, J=7.9, 4H), 8.75-9.35 (broad m, 4H)

Example 6: Synthesis of In/Out-Diphosphonate Calixpyrrole (Ib8)

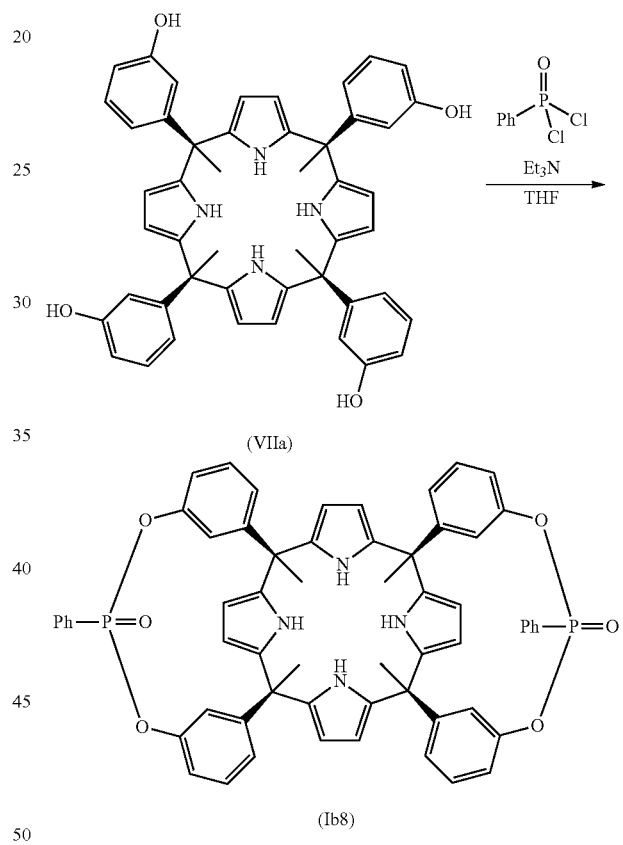

Triethylamine (1.5 mL, 10.75 mmol, 20 equiv.) followed by phenylphosphonic dichloride (0.2 mL, 1.43 mmol, 2.6 equiv.) were added to a solution of starting tetrahydroxy calixpyrrole (VIIA) (406 mg, 0.55 mmol, 1 equiv.) in THF (anhydrous and degassed, 20 mL, 0.027 M) stirring at room temperature under Argon atmosphere. The reaction was stirred at room temperature for 16 hours during which time a white precipitate was formed in the reaction mixture. At this time the reaction mixture was brought to≈pH 2 with 1M HCl(aq) and the resultant mixture was extracted with CH$_2$Cl$_2$ (3×100 mL). The organic extracts were combined, dried over Na$_2$SO$_4$ and evaporated under vacuum to give a white powder. The reaction crude was first purified by column chromatography (SiO$_2$; CH$_2$Cl$_2$: MeOH 99:1) in order to remove the oligomers/polymers formed during the reaction with 60% overall yield. The fraction containing the three diasteromers was purified by semipreparative HPLC (Spherisorb silica 250×20 mm, 5 μm; SiO$_2$; CH$_2$Cl$_2$: MeOH 99:1) to yield each separated isomer Ib9, Ib8 and Ib7 as white solids (Retention times: 4.8 minutes, 6.19 minutes and 9.8 minutes, respectively). The three isomers can be further purified by crystallization from acetonitrile.

In/Out-Diphosphonate Calixpyrrole (Ib8)

1H NMR (400 MHz, CDCl3, 25° C.) δ (ppm) 1.99 (s, 6H), 2.00 (s, 6H), 5.68 (t, J=3.0 Hz, 2H), 5.77 (t, J=3.0 Hz, 2H), 6.13 (d, J=2.6 Hz, 2H), 6.18 (d, J=2.6 Hz, 2H), 6.76-6.80 (m, 2H), 6.90-6.97 (m, 4H), 7.00 (d, J=7.9, 2H), 7.07-7.15 (m, 6H), 7.22 (t, J=7.9 Hz, 2H), 7.49-7.69 (m, 6H), 7.83 (s, 1H), 7.95-8.03 (m, 4H), 8.07 (s, 2H), 8.48 (s, 1H).

In/In-Diphosphonate Calixpyrrole (Ib7)

$^1$H-NMR (500 MHz, CD$_2$Cl$_2$, 25° C.): δ (ppm)=8.18 (bs, 4H), 8.04 (m, J=14 Hz, J=7.3 Hz, J=1.2 Hz, 4H), 7.71 (m, J=7.3 Hz, J=1.2 Hz, 2H), 7.61 (m, J=7.3 Hz, J=4.8 Hz, 4H), 7.24 (t, J=7.9 Hz, 4H), 7.02 (d, J=7.9 Hz, 4H), 6.96 (d, J=7.9 Hz, H), 6.94 (s, 4H), 6.17 (d, J=2.55 Hz, 4H), 6.05 (d, J=2.55 Hz, 4H), 1.80 ppm (s, 12H).

Out/Out-Diphosphonate Calixpyrrole (Ib9)

$^1$H-NMR (500 MHz, CD2Cl2, 25° C.): δ (ppm)=8.04 (bs, 2H), 8.00 (m, J=14 Hz, J=7.3 Hz, J=1.2 Hz, 4H), 7.70 (m, J=7.3 Hz, J=1.2 Hz, 2H), 7.60 (m, J=7.3 Hz, J=4.8 Hz, 4H), 7.49 (bs, 2H), 7.26 (t, J=7.7 Hz, 4H), 7.22 (d, J=7.7 Hz, 4H), 7.18 (s, 4H), 6.86 (d, J=7.7 Hz, 4H), 6.32 (d, J=2.65 Hz, 4H), 5.50 (bs, 4H), 2.07 (s, 12H).

Example 6 bis: Synthesis of bisthiophosphonate calix[4]pyrrole Ib11, Ib12, and Ib13

The starting calix[4]pyrrole (VIIA) (0.4 g, 0.54 mmol) was dissolved in pyridine (42 mL, 52 mmol) (dried over CaH and freshly distilled) under argon atmosphere forming a colorless solution. Then, phenylphosphine dichloride (150 uL, 1.11 mmol) was added and the reaction mixture turned yellow. With time a white precipitate appeared. 1 h and 30 minutes after addition of the phosphine, the reaction mixture was heated at 70° C. and stirred for additional 30 minutes. After that time, sulfur (55.4 mg, 0.22 mmol) was added and the reaction was left under stirring at the same temperature overnight. Next day, the pyridine was removed under reduced pressure, and the crude was dissolved in 20 mL of dichloromethane (DCM). 10% HCl$_{aq}$ was added, and the aqueous phase was extracted with DCM 3×20 mL. Then the DCM extracts were combined and washed with 10% HCl$_{aq}$ 3×20 mL to remove the remaining pyridine. The DCM phase was dried over Na$_2$SO$_4$, filtered and concentrated under vacuum, yielding 0.51 g of crude. The crude of the reaction was purified by column chromatography (20 g of SiO$_2$) and 6:4 dichloremethane (DCM):hexane as eluent mixture. compound (Ib11) eluted first (Rf=0.57, 109.1 mg 20% yield) followed by (Ib12) (Rf=0.38, 213.8 mg 39% yield) and (Ib13) (Rf=0.19, 82.9 mg, 15% yield).

Ib11 (i/i):

1H NMR (400 MHz, CDCl3, 25° C.): δ (ppm) 8.12-8.02 (m, 6H), 7.96 (bs, 2H), 7.65-7.59 (m, 2H), 7.58-7.52 (m, 4H), 7.18 (t, J=7.89 Hz, 4H), 6.94 (d, J=7.89 Hz, 4H), 6.84 (d, J=7.89 Hz, 4H), 6.7 (s, 4H), 6.17 (d, J=2.57 Hz, 4H), 5.99 (s, 4H), 1.99 (s, 12H); 31P{1H}NMR (161.9 MHz, CDCl3, 25° C.): δ (ppm) 85.6 (s); HRMS(ESI-TOF) m/z: [M+Na]+ calcd for C60H50N4O4NaP2S2=1039.2641; Found 1039.2667.

Ib12 (i/o):

1H NMR (400 MHz, CDCl3, 25° C.): δ (ppm) 8.25 (bs, 1H), 8.15-8.06 (m, 6H), 7.89 (bs, 1H), 7.67-7.52 (m, 6H), 7.28-7.09 (m, 10H), 6.88 (d, J=7.77 Hz, 2H), 6.82 (s, 2H), 6.77 (d, J=7.77 Hz, 2H), 6.21 (d, J=2.54 Hz, 2H), 6.16 (d, J=2.54 Hz, 2H), 5.65-5.60 (m, 2H), 5.59-5.56 (m, 2H), 2.06 (s, 6H), 2.05 (s, 6H); 31P{1H}NMR (161.9 MHz, CDCl3, 25° C.): δ (ppm) 85.0 (s), 79.0 (s) HRMS(ESI-TOF) m/z: [M+H]+ calcd for C60H51N4O4P2S2=1017.2821; Found 1017.2838.

Ib13 (o/o):

1H NMR (400 MHz, CDCl3, 25° C.): δ (ppm) 8.09-8.02 (m, 4H), 7.85 (bs, 2H), 7.64-7.58 (m, 2H), 7.57-7.49 (m, 4H), 7.31 (bs, 2H), 7.29 (d, J=8.25 Hz, 4H), 7.20 (t, J=8.25 Hz, 4H), 7.05 (s, 4H), 6.75 (d, J=8.05 Hz, 4H), 6.2 (d, J=2.62 Hz, 4H), 5.26 (d, J=2.62 Hz, 4H), 2.06 (s, 12H); 31P{1H}NMR (161.9 MHz, CDCl3, 25° C.): δ (ppm) 78.9 (s); HRMS(ESI-TOF) m/z: [M+H]+ calcd for C60H51N4O4P2S2=1017.2821; Found 1017.2872.

Example 7: Synthesis of Monomethyl-Monophosphonate-Bridged Calixpyrrole (Type Ib1)

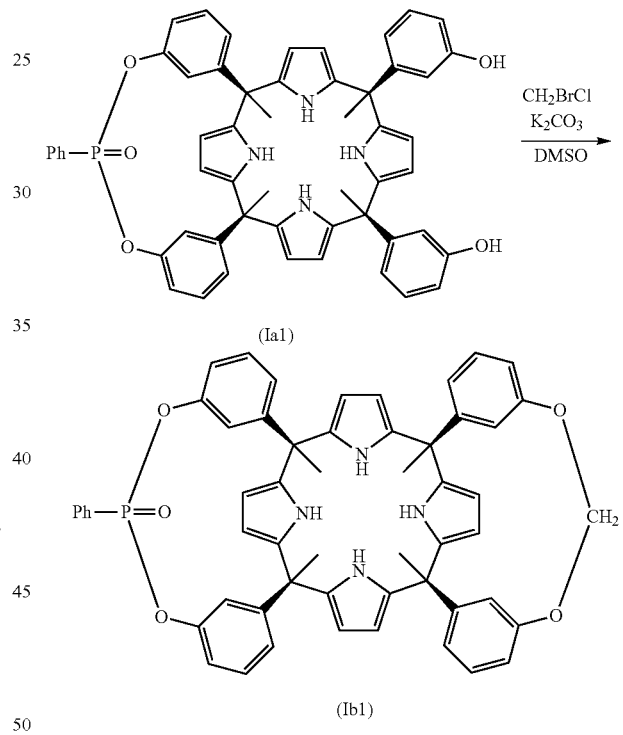

Single in-phosphonate-bridge calixpyrrole (Ia1) (26 mg, 30 μmol, 1 equiv.) and K$_2$CO$_3$ (33 mg, 241 μmol, 8 molar equiv.) were added to a sealable tube. This tube was placed under vacuum for 10 hours to remove as much water as possible from the reagents. The sealed tube was purged with Argon 3 times. DMSO (3 mL, 10 mM) was added followed by bromochloromethane (10 μL, 151 μmol, 5 equiv.) and the tube was sealed. The turbid reaction mixture was placed in an oil bath set to 100° C. and stirred for 1 hour. The reaction mixture was cooled, the sealed tube was opened and the mixture was brought to≈pH 2 with 1M HCl(aq). The resultant mixture was extracted with CH$_2$Cl$_2$ (2×5 mL). The combined organic extracts were washed with water, dried over Na$_2$SO$_4$, and the CH$_2$Cl$_2$ was evaporated to give a light beige powder. This material was purified by column chromatography (silica gel, CH$_2$Cl$_2$ to 5% MeOH in CH$_2$CO$_2$, Rf of product is 0.70 with 1% MeOH i, n CH$_2$Cl$_2$ eluent). The fractions containing only the desired product were collected together and evaporated under vacuum to give pure material as a white powder, 15 mg (57% yield).

Monomethyl-Monophosphonate-Bridged Calixpyrrole (Ib1)

1H NMR (500 MHz, CDCl3, 25° C.) δ (ppm) 1.94 (s, 6H), 1.98 (s, 6H), 5.56 (d, J=6.9, 1H), 5.79 (d, J=7.0 Hz, 1H), 5.81 (t, J=3.1, 2H), 5.84 (t, J=3.1, 2H), 6.07 (d, J=2.6 Hz, 2H), 6.14 (d, J=2.6, 2H), 6.58 (t, J=2.2, 2H), 6.84 (d, J=7.8, 2H), 6.88 (dd, J=8.0, 2.4, 2H), 6.95-6.99 (m, 4H), 7.04 (d, J=8.0, 2H), 7.12 (t, J=7.9, 2H), 7.24 (t, J=7.8, 2H) 7.57 (td, J=7.6, 4.8, 2H), 7.67 (t, J=7.5, 1H), 7.84 (s, 1H), 7.97-8.04 (m, 4H), 8.50 (s, 1H).

Analogously to this process, the stereoisomer (Ib2) was obtained as a by-product of this reaction that can be separated from (Ib1) during the step of column chromatography under the conditions pointed out above.

Analogously, the compound (Ib3) can be obtained following the same process as the one for (Ib1) by replacing compound (Ia1) with a compound of formula (Ia4), obtainable by reaction of a compound of formula (VIIA) with dichlorophosphoramide, as described in Example 4.

(Ia4)

Analogously, the compound (Ib4) can be obtained following the same process as the one for (Ib1) by replacing compound (Ia1) with a compound of formula (Ia5), obtainable by reaction of a compound of formula (VIIA) with sulfuryl chloride, as described in Example 4.

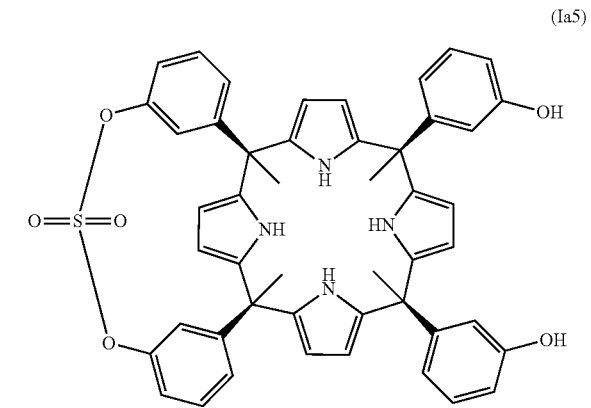 [SMILES: C[C@]1(c2cccc(O)c2)c2ccc([nH]2)[C@@](C)(c2cccc(O)c2)c2ccc([nH]2)[C@@]2(C)c3cccc(c3)OS(=O)(=O)Oc3cccc(c3)[C@@](C)(c3ccc1[nH]3)c1ccc2[nH]1]

(Ia5)

Example 8: Synthesis of In/Out/Out/Out-Tetraphosphonate Calixpyrrole (Type Ic1)

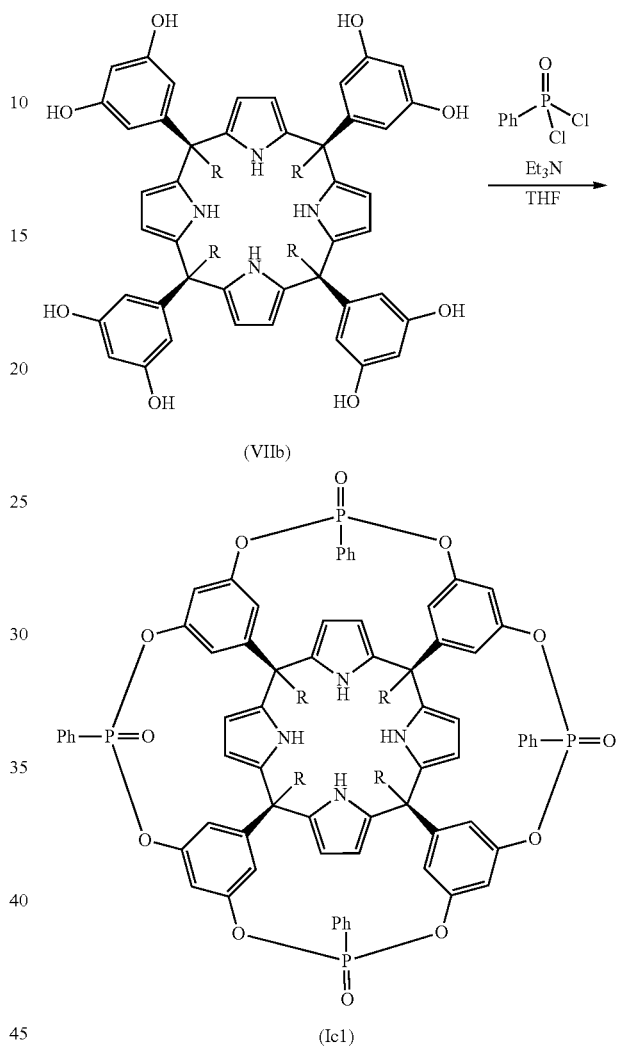

Triethylamine (1 mL, 7.03 mmol, 20 equiv.) followed by phenylphosphonic dichloride (0.25 mL, 1.76 mmol, 5 equiv.) were added to a solution of starting octahydroxy calixpyrrole VIIb (R=CH$_3$, 500 mg, 0.35 mmol, 1 equiv.) in THF (anhydrous and degassed, 10 mL, 0.035 M) stirring at room temperature under Argon atmosphere. The reaction was stirred at room temperature for 2 hours during which time a white precipitate was formed in the reaction mixture. All solvent was removed from the reaction under vacuum and water (50 mL) was added. A grey precipitate was formed in the water mixture. This precipitate was collected by filtration. This material was purified by column chromatography (silica gel, CH$_2$Cl$_2$) collecting the fractions containing the compounds that eluted first. These fractions were purified by semipreparative HPLC (Spherisorb silica 250×20 mm, 5 μm; SiO$_2$; CH$_2$Cl$_2$: Hexane 60:40; flow rate: 15 mL/min) to yield the desired product as a white solid (Retention time: 5.3 minutes). The product was further purified by recrystallization from acetonitrile to give the pure product 60 mg, (9%).

In/Out/Out/Out-Tetraphosphonate Calixpyrrole (Type Ic1)

$^1$H NMR (400 MHz, CDCl3, 25° C.): δ (ppm) 7.97 (m, 8H), 7.79 (t, J=2.3, 1H), 7.76 (t, J=3.0, 2H), 7.72 (t, J=2.3, 1H), 7.66 (m, 4H), 7.55 (m, 8H), 7.46 (t, J=2.0, 2H), 7.46 (t, J=2.0, 2H), 7.46 (t, J=2.0, 2H), 6.81 (t, J=2.0, 2H), 6.77 (t, J=3.3, 2H), 6.55 (t, J=3.3, 2H), 6.18 (d, J=2.3, 2H), 6.15 (t, J=3.0, 2H), 6.12 (t, J=3.0, 2H), 6.08 (d, J=2.3, 2H), 2.45 (m, 8H), 1.27 (m, 80H), 0.89 (t, J=7.0, 12H).

Example 8 bis

Synthesis of Tetraphosphonate Calixpyrroles (Ic3) and (Ic4)

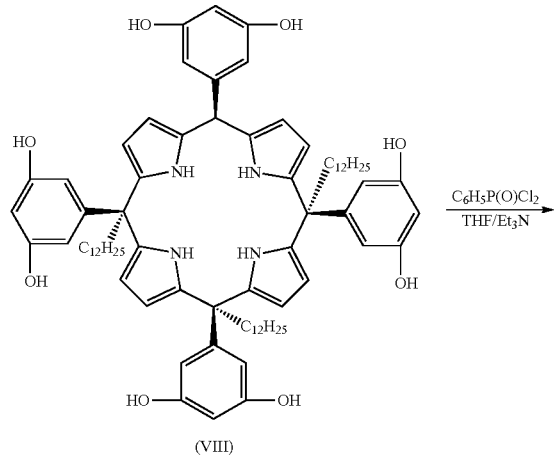

(VIII) → Ic3, Ic4

$C_6H_5P(O)Cl_2$
THF/Et$_3$N

To a solution of calix[4]pyrrole (VIII) (500 mg, 0.352 mmol) in dry THF (10 mL) and freshly distilled triethylamine (0.980 mL, 7.03 mmol), phenylphosphonic dichloride (0.247 mL, 1.758 mmol) was added dropwise under argon atmosphere. The reaction mixture was stirred for 2 hrs at room temperature. The solvent was removed in vacuo and water (50 mL) was added. The grey precipitate was filtered off and purified by column chromatography (SiO$_2$; CH$_2$Cl$_2$) in order to remove the oligomers/polymers formed during the reaction. The fraction containing the two diastereomers was purified by semipreparative HPLC (Spherisorb silica 250×20 mm, 5 μm; SiO$_2$; CH$_2$Cl$_2$: Hexane 60:40; flow rate: 15 mL/min) to yield each separated isomer Ic3 and Ic4 as white solids (Retention times: 4.3 minutes and 5.3 minutes, respectively). The isomers can be further purified by crystallization from acetonitrile.

Experimental Data for Ic3:

$_1$H-NMR (400 MHz, CDCl$_3$, 25° C.): δ (ppm)=7.94 (m, 8H), 7.65 (m, 4H), 7.53 (m, 8H), 7.53 (bs, 4H), 7.37 (d, $_4J_{H—H}$~1.75 Hz, 8H), 6.56 (t, $_4J_{H—H}$~1.75 Hz, 4H), 6.17 (d, $_4J_{H—H}$~2.27 Hz, 8H), 2.45 (m, 8H), 1.27 (m, 80H), 0.88 (t, $_3J_{H—H}$~7.0 Hz, 12H). $_{31}$P-NMR: δ (ppm)=13.63. $_{13}$C-NMR: δ (ppm)=151.5, 151.4, 136.2, 133.4, 131.4, 131.3, 128.8, 128.6, 116.8, 106.6, 49.0, 39.0, 31.9, 30.2, 29.8, 29.7, 29.6, 29.3, 24.7, 22.7, 14.3. HR-MALDI-MS: m/z calculated for C$_{116}$H$_{144}$N$_4$O$_{12}$P$_4$1908.9731, found 1908.9699; FT-IR ν (cm$_{-1}$) 2921-2851, 1592, 1426, 1293.

Experimental data for Ic4 (white powder, 9%). $_1$H-NMR (400 MHz, CDCl$_3$, 25° C.): δ (ppm)=7.97 (m, 8H), 7.79 (t, $_4J_{H—H}$~2.3 Hz, 1H), 7.76 (t, $_4J_{H—H}$~3.0 Hz, 2H), 7.72 (t, $_4J_{H—H}$~2.3 Hz, 1H), 7.66 (m, 4H), 7.55 (m, 8H), 7.46 (t, $_4J_{H—H}$~2.0 Hz, 2H), 7.46 (t, $_4J_{H—H}$~2.0 Hz, 2H), 6.81 (t, $_4J_{H—H}$~2.0 Hz, 2H), 6.77 (t, $_4J_{H—H}$~3.3 Hz, 2H), 6.55 (t, $_4J_{H—H}$~3.3 Hz, 2H), 6.18 (d, $_4J_{H—H}$~2.3 Hz, 2H), 6.15 (t, $_4J_{H—H}$~3.0 Hz, 2H), 6.12 (t, $_4J_{H—H}$~3.0 Hz, 2H), 6.08 (d, $_4J_{H—H}$~2.3 Hz, 2H), 2.45 (m, 8H), 1.27 (m, 80H), 0.89 (t, $_3J_{H—H}$~7.0 Hz, 12H); $_{31}$P-NMR: δ (ppm)=14.37, 12.96. $_{13}$C-NMR: δ (ppm)=151.8, 151.4, 151.3, 151.2, 149.1, 149.0, 136.8, 136.4, 136.1, 133.6, 133.4, 131.5, 131.4, 131.3, 131.2, S5 131.1, 128.9, 128.7, 128.6, 128.0, 127.9, 127.1, 126.4, 126.3, 125.5, 118.6, 118.0, 117.5, 117.4, 112.1, 112.0, 108.9, 108.8, 108.7, 106.0, 105.8, 105.7, 105.5, 48.9, 48.8, 39.0, 38.9, 31.9, 30.2, 30.1, 29.9, 29.8, 29.6, 29.5, 29.3, 24.8, 24.6, 22.7, 14.1. HRMALDI-MS: m/z calculated for C$_{116}$H$_{144}$N$_4$O$_{12}$P$_4$1908.9731, found 1908.9866; FT-IR ν(cm$_{-1}$) 2921-2850, 1593, 1430, 1294.

Example 9: Membrane Composition 3.63 mg of creatinine ionophore (Ib1), 1.00 mg of cation-exchanger salt (potassium tetrakis[3,5-bis(trifluoromethyl)phenyl]borate (KTFPB)), 31.37 mg of polymeric matrix polyvinyl chloride (PVC) of high molecular weight (manufacturer's reference 81387-250G) and 64.00 mg of plasticizer o-nitrophenyl octyl ether (o-NPOE) are mixed in 1 mL of tetrahydrofuran (THF), as shown in the table below (Table 1). This mixture is vigorously shaken in a bath sonicator for 30 minutes until obtaining a transparent solution ready for deposition.

The same membrane composition as above was prepared but in the absence of the ionophore (hereinafter also referred as "blank membrane").

TABLE 1

Composition of a blank and a creatinine potentiometric sensing membrane.

| | % weight | |
|---|---|---|
| Compound | Blank membrane | Creatinine membrane |
| Ionophore | — | 3.63 |
| KTFPB | 1.00 | 1.00 |
| PVC | 33.0 | 31.37 |
| o-NPOE | 66.0 | 64.00 |
| THF (solvent) | 1 mL | 1 mL |

All the components for each membrane were simply mixed and stored for their posterior use in the manufacture of the electrode.

Analogously, membranes comprising ionophores (Ia1), (Ib7), (Ib8), (Ib9), (Ib10), (Ib11), (Ib12), (Ib13), (Ic3) and (Ic4) were prepared following the same procedure as the one followed for the membrane comprising ionophore (Ib1), but using the amounts (expressed in milligrams) specified in Table 1bis below:

TABLE 1bis

| Compound | Blank | Ia1 | Ib7 | Ib8 | Ib9 | Ib10 | Ib11 |
|---|---|---|---|---|---|---|---|
| Ionophore | — | 3.2 | 3.63 | 3.63 | 3.63 | 2.75 | 3.7 |
| KTFPB | 1 | 1 | 1 | 1 | 1 | 1 | 1 |
| PVC | 33 | 32 | 31.37 | 31.37 | 31.37 | 32.25 | 31.7 |
| o-NPOE | 66 | 63.8 | 64 | 64 | 64 | 64 | 63.6 |

TABLE 1bis-continued

| Compound | Blank | Ib12 | Ib13 | Ic3 | Ic4 |
|---|---|---|---|---|---|
| Ionophore | — | 3.7 | 3.7 | 4.02 | 4.02 |
| KTFPB | 1 | 1 | 1 | 1 | 1 |
| PVC | 33 | 31.7 | 31.7 | 31.98 | 31.98 |
| o-NPOE | 66 | 63.6 | 63.6 | 63 | 63 |

In 1 mL THF

Example 10: Manufacturing of the Electrode

The body of each creatinine-selective electrode was made of glassy carbon (HTW) (GC) rod (length=50 mm, diameter=3 mm) inserted into a Teflon body (RS Amidata) (length=40 mm, outer diameter=6 mm). The GC surface was polished with alumina of different sizes (25, 1 and 0.03 μm, Buehler, USA), with an active surface of 7 mm$^2$.

Solid-Contact Ion-Selective Electrode:

The next step is to drop-cast 50 μL of the polymeric membrane solution obtained in Example 9, onto the above conductor and let the solvent evaporate for up to 2 hours. Once the membrane was fully dried onto the conductor, the membrane was subjected to a conditioning step by submerging it into a 10 mM acetic acid/acetate buffer solution containing 10 mM creatinine for 1 hour. This conditioning step was suitable in order to obtain stable measurements when calibrating and measuring with creatinine as well as real samples, respectively.

The same protocol was repeated for the blank membrane composition as well as for the membrane compositions provided in Table 1bis above.

Ion-Selective Electrode with Inner Filling Solution Electrode:

In the case of ion-selective electrode with inner filling solution, 50 μL of the polymeric membrane obtained in previous Example 9, were drop-casted on a glass-casting plate. The membrane was gently peeled off and placed in the membrane packing piece of the electrode (Electrode Body ISE, 45137 Sigma Aldrich) and finally pressed with the membrane housing to put the membrane in contact with the inner electrolyte solution, which is 10 mM of creatinine in 10 mM acetic acid/acetate buffer solution. The final step was the calibration step, wherein the polymeric membrane was placed in contact with a 10 mM creatinine solution and a 10 mM acetic acid/acetate buffer solution to obtain stable potential readings without noise coming from the first contact of the membrane to the solution.

The same protocol was followed with the blank membrane composition.

Calibration measurements: The measurements were carried out with an acetic acid/acetate buffer solution of 10 mM and the concentration of creatinine was increased by adding amounts of creatinine standards.

Example 11: Design of a Potentiometric Cell Device

The potentiometric cell assembly consists basically in measuring the potential generated between two electrodes: a Ag/AgCl reference electrode (A double junction Ag/AgCl/KCl 3 M reference electrode containing 1 M LiAcO as electrolyte bridge, type 6.0729.100 was employed (Metrohm AG)) that maintains a constant potential, due to the presence of a high concentrated KCl electrolyte coupled to a bridge electrolyte and the sample through a liquid junction; and an ion-selective electrode, which included the creatinine selective membrane or the blank membrane. This ion-selective electrode can be either any of the polymeric membranes of Example 9 (Tables 1 and 1 bis) in contact with an inner filling solution of 10 mM of creatinine with 10 mM buffer solution at in contact with an Ag/AgCl wire, or the polymeric membrane in contact with a glassy carbon rod as a solid-state ion-selective electrode, in direct contact with the sample.

The measuring circuit is assembled in order to be able to record the electromotive force generated between these electrodes by a voltmeter, which may explain the presence or absence of the target analyte.

Example 12: Limit of Detection/Linear Range/Response Time

Stock solutions of creatinine at different concentrations from $10^{-7}$ to $10^{-2}$ M were prepared. Then, potentiometric measurements were made using the potentiometric cells comprising the solid electrode either with the membrane comprising the compound of the invention Ib1 or the blank membrane. The results are summarized in FIG. 1.

Additions of one logarithmic activity unit were added into the potentiometric cell in order to obtain a potentiometric trace of the sensor as well as a calibration curve, where linear regression and performance of the sensor can be tested out.

Figure 2:
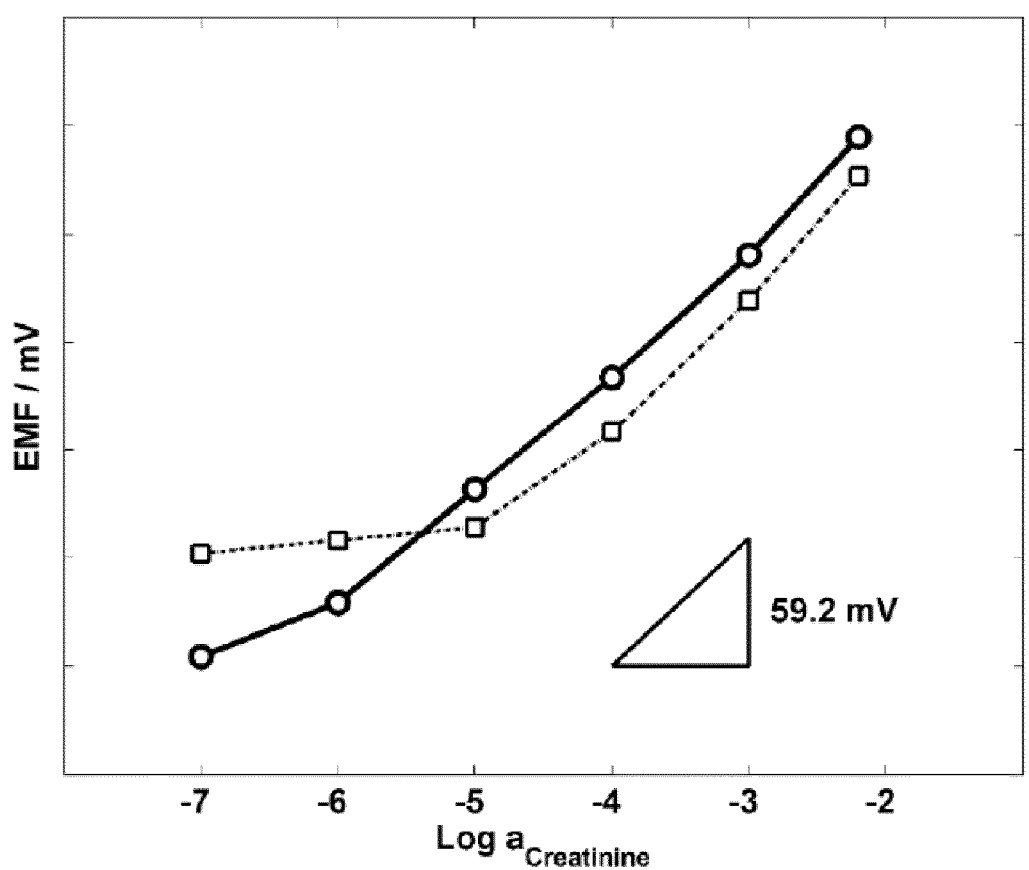
FIG. 2 illustrates the linear dependence for the response of the ion-selective electrode described in this invention (line, circles) and a sensor built without the ionophore (dashed line, squares) between potential (mV) as a function of the logarithm of the activity of creatinine ion in the solution. As it can be seen in this figure, the receptor for creatinine allows detecting creatinine at lower activities than without receptor.
Figure 3:
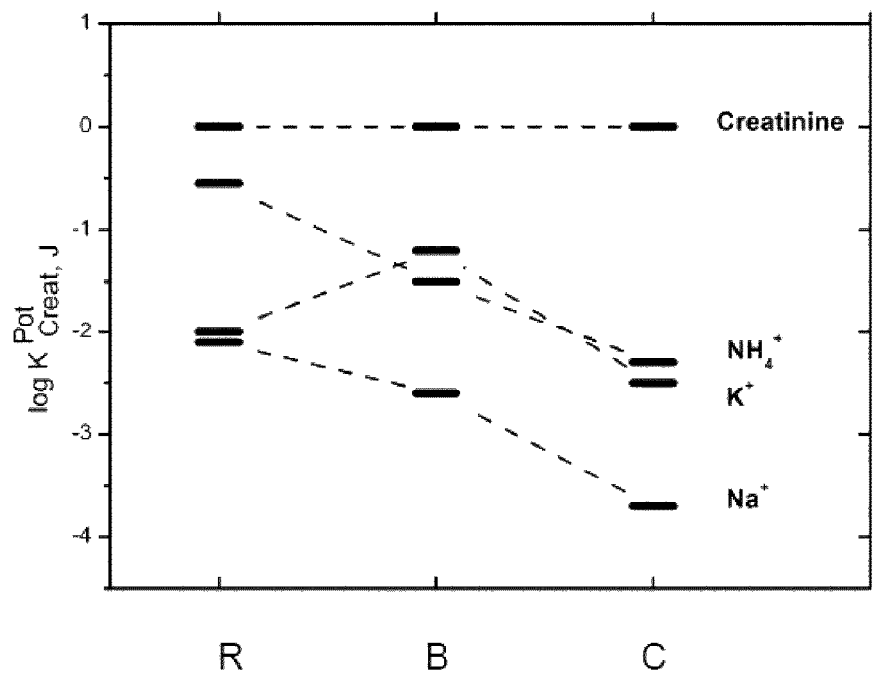
FIG. 3 shows the potentiometric selectivity coefficients (log K Creat) required for real samples measurements (R), calculated by separate solution method and expressed as log $K^{POT}_{A,B}$, obtained for the receptor-less ion-selective electrode (B=blank) and finally the creatinine ion-selective electrode of this invention (C).

A linear regression was made from the data obtained, obtaining FIG. 2. From this figure the parameters shown in Table 2 below were obtained:

TABLE 2

| Potentiometric parameters of the blank and the creatinine polymeric membrane | | |
|---|---|---|
| Parameter | Blank membrane | Creatinine membrane |
| Sensitivity (mV/log $a_{creatinine}$) | 58.4 ± 0.5 | 54.2 ± 0.6 |
| Limit of detection (M) | $10^{-4.7}$ | $10^{-6.2}$ |
| Linear range (M) | $10^{-4}$-$10^{-2}$ | $10^{-6}$-$10^{-2}$ |
| Response time (s) | 15 | 10 |

$a_{creatinine}$ = concentration of creatinine

Sensitivities close to ideal 59.2 mV/log $a_{creatinine}$ mean that the sensor is sensing creatinine following the analytical Nernst equation.

$$E=E^0-0.0592 \log a_{creatinine}$$

As it can be concluded from Table 2, including a compound of the invention the limit of detection is improved in more than one order and the sensitivity is appropriate (adjusted to Nernstian response). The fact that the response is linear for a broader range of concentration is indicative of its stability and usability as potentiometric sensor.

Example 13: Interferences

In this section the selectivity of the electrode of the invention was determined measuring the potential value in different solutions prepared as in the example above. The potentiometric cell used was the one with the solid-contact ion-selective electrode as disclosed in Example 10 with ionophore (Ib1).

The calculation of the selectivity coefficients is achieved by the separate solution method (SSM) following the protocol disclosed by Umezawa, Y. et al., (Umezawa et al., " " Pure Appl. Chem. 2000, 72, 1851-2082). where the ion-selective electrode is calibrated with the selected interferences at 10 mM. The selectivity coefficients are calculated against the main cations present in biological fluids—urine, serum and plasma—(see Table 3). Comparing the calculated coefficients with the required ones is the first step to demonstrate that the sensor may predict creatinine accurately in real sample measurements.

$$\log K_{A,B}^{POT} = \frac{(E_B - E_A)z_A F}{2.303\, RT} + \left(1 - \frac{z_A}{z_B}\right) \log a_A$$

where:
$E_A$ and $E_B$ stand for the potential contribution of analyte and interference, respectively.
$a_A$ and $z_A$ are the activity and the charge of the analyte, respectively.
$a_B$ and $z_B$ are the activity and the charge for the interfering ion.
R is the universal gas constant (8.31 J mol$^{-1}$K$^{-1}$), T is temperature (K) and finally F is the Faraday constant (96485 A mol$^{-1}$).

The same protocol was followed with the potentiometric cell comprising the membrane blank.

TABLE 3

Selectivity values calculated by separate-solution method expressed as log $K^{POT}_{creatinine}$.

| Interferent | Blank sensor | Creatinine sensor | Typically Required |
|---|---|---|---|
| Citric Acid | −2.9 ± 0.1 | −4.6 ± 0.2 | 0.54 |
| NaHCO$_3$ | −2.6 ± 0.1 | −4.0 ± 0.1 | −0.55 |
| Urea | −2.6 ± 0.1 | −4.3 ± 0.1 | −1.30 |
| Ca$^{2+}$ | −3.4 ± 0.1 | −4.8 ± 0.1 | 0.52 |
| Na$^+$ | −2.6 ± 0.1 | −3.7 ± 0.1 | −2.1 |
| NH$_4^+$ | −1.5 ± 0.1 | −2.3 ± 0.1 | −0.55 |
| K$^+$ | −1.2 ± 0.1 | −2.5 ± 0.1 | −2.0 |
| Creatine | −2.4 ± 0.1 | −3.5 ± 0.1 | — |

A negative value is indicative of the selectivity of the sensor, and the more negative the value is, the more selective is the electrode. From Table 3 it can be concluded that the sensor comprising the compound Ib1 of the invention is more selective, particularly in terms of the selectivity towards potassium, which is a serious interference commonly found in biological fluids.

The "required selectivity coefficient" calculation is based on the known concentration range of the analyte and the interfering ion in the sample (biological fluids, such as urine).

The required selectivity coefficients were calculated using the following equation:

Log $K$ = log $C_B$ − log $C_A$

Where $C_B$ and $C_A$ stand for the concentration of the interfering anion and the analyte, respectively.

Considering that the values of the coefficients are inferior to the required ones, particularly for K$^+$, many of the interferences may not affect the measurements in real samples.

The same protocol was followed with the membrane compositions listed in Table 1bis in the form of electrodes as disclosed in Example 10. The results are summarized in Table 3bis below. Again, the coefficient values obtained were inferior to the required ones, which is an indicia that interferences may not affect creatinine measurements in real samples. Therefore, from these data it can be concluded that the compounds of the invention are creatinine selective.

TABLE 3bis

| | No ionophore | Ia1 | Ib7 | Ib8 | Ib9 | Req. |
|---|---|---|---|---|---|---|
| Citric acid | −2.9 ± 0.1 | −3.8 ± 0.1 | −3.6 ± 0.1 | −2.8 ± 0.1 | −3.7 ± 0.1 | 0.54 |
| NaHCO$_3$ | −2.6 ± 0.1 | −3.9 ± 0.1 | −3.5 ± 0.1 | −3.1 ± 0.1 | −3.2 ± 0.1 | −0.55 |
| Urea | −2.6 ± 0.1 | −3.7 ± 0.1 | −3.4 ± 0.1 | −3.6 ± 0.1 | −3.7 ± 0.1 | −1.30 |
| Ca$^{2+}$ | −3.4 ± 0.1 | −4.3 ± 0.1 | −3.9 ± 0.1 | −4.0 ± 0.1 | −3.7 ± 0.1 | 0.52 |
| Na$^+$ | −2.6 ± 0.1 | −3.1 ± 0.1 | −3.2 ± 0.1 | −2.6 ± 0.1 | −2.9 ± 0.1 | −2.1/−1.2 |
| NH$_4^+$ | −1.5 ± 0.1 | −2.1 ± 0.1 | −2.2 ± 0.1 | −1.9 ± 0.1 | −1.6 ± 0.1 | −0.55 |
| K$^+$ | −1.2 ± 0.1 | −2.1 ± 0.1 | −2.0 ± 0.1 | −2.3 ± 0.1 | −2.0 ± 0.1 | −1.5 |
| Creatinine | −2.4 ± 0.1 | −3.1 ± 0.1 | −2.8 ± 0.1 | −2.4 ± 0.1 | −2.9 ± 0.1 | — |

| | No ionophore | Ib13 | Ic3 | Ic4 | Req. |
|---|---|---|---|---|---|
| Citric acid | −2.9 ± 0.1 | −3.9 ± 0.1 | −3.6 ± 0.1 | −3.5 ± 0.1 | 0.54 |
| NaHCO$_3$ | −2.6 ± 0.1 | −3.6 ± 0.1 | −3.3 ± 0.1 | −3.2 ± 0.1 | −0.55 |
| Urea | −2.6 ± 0.1 | −4.8 ± 0.1 | −3.2 ± 0.1 | −3.2 ± 0.1 | −1.30 |
| Ca$^{2+}$ | −3.4 ± 0.1 | −3.9 ± 0.1 | −3.9 ± 0.1 | −3.9 ± 0.1 | 0.52 |
| Na$^+$ | −2.6 ± 0.1 | −3.0 ± 0.1 | −3.1 ± 0.1 | −3.0 ± 0.1 | −2.1/−1.2 |
| NH$_4^+$ | −1.5 ± 0.1 | −1.7 ± 0.1 | −2.0 ± 0.1 | −2.0 ± 0.1 | −0.55 |
| K$^+$ | −1.2 ± 0.1 | −1.6 ± 0.1 | −1.8 ± 0.1 | −1.7 ± 0.1 | −1.5 |
| Creatinine | −2.4 ± 0.1 | −3.5 ± 0.1 | −2.6 ± 0.1 | −2.6 ± 0.1 | — |

Example 14: Real Sample Measurement

The creatinine selective polymeric membrane can be used to facilitate daily measurements by physicians, technicians, among others in the laboratories that require rapid, simple and easy-to-use instrumentation to obtain analytical results.

The electrode used was the solid type with the ionophore of the invention of formula (Ib1).

Urine

The sample is collected at any time followed by a 100 fold dilution with a 0.05 M buffer at pH around 3.7. This step ensures the creatinine to be charged. After that, the potential generated can be recorded with the high-input impedance voltmeter. Electrodes must be cleaned in between measurements with abundant distilled water.

The same samples were also analysed using Jaffé method using the kit commercialized by Sigma-Aldrich, with manufacturer's reference MAK080-1KT.

Figure 4:
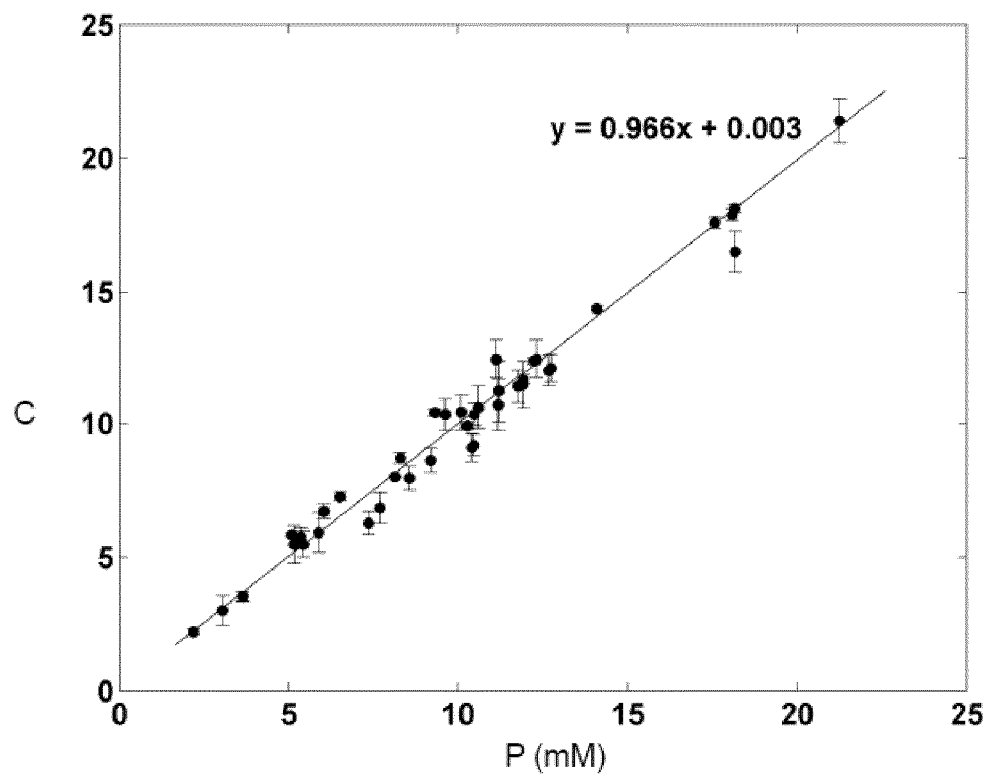
FIG. 4 illustrates the linear relationship between creatinine values obtained for urine samples potentiometrically of the invention (X axis, "P") and the creatinine values obtained with the Jaffé colorimetric method (Y axis, "C").

The results are summarized in FIG. 4.

Plasma

In the case of plasma and serum, the sample must be also diluted although in this case the dilution is only 10 times since the amount in both samples is 2 times lower. The sample is collected and diluted 1:10 with a pH 3.7 buffer 0.05 M to obtain the charged creatininium ion. As in the previous sample, the potential is therefore recorded with the voltmeter. Longer response times have been observed after several serum/plasma samples measurements.

The same samples were also analysed using Jaffé method as above.

The results are summarized in Table 4:

TABLE 4

Creatinine values obtained from different plasma samples for the standard method (Jaffé) and the potentiometric method developed here.

| Plasma samples | Jaffé Method (mM) | Potentiometric method (mM) |
| --- | --- | --- |
| 1 | 0.33 | 0.36 |
| 2 | 0.57 | 0.62 |
| 3 | 0.31 | 0.33 |
| 4 | 0.24 | 0.29 |

As one can see, the electrode of the invention is a reliable tool in the measurement of creatinine in real samples.

REFERENCES CITED IN THE APPLICATION

Jacobs, R. M.; et al., "Effects of Interferents on the Kinetic Jaffe Reaction and an Enzymatic Colorimetric Test for Serum Creatinine concentration Determination in Cats, Cows, Dogs and Horses", E. *Can. J. Vet. Res.,* 1991, v. 55, 150-154.

Dimeski, C et al., "Ion Selective Electrodes (ISEs) and interferences—A review", *Clin. Chim. Acta,* 2010, v. 411, 309-317.

Meyerhoff, M. et al., "An activated enzyme electrode for creatinine", *Anal. Chim. Acta,* 1976, v. 85, 277-285.

Bühlmann, P. et al., "Influence of Natural, Electrically Neutral Lipids on the Potentiometric Responses of Cation-Selective Polymeric Membrane Electrodes", *Anal. Chem.,* 2001, v. 73, 3199-3205.

Hassan, S. "Novel Biomedical Sensors for Flow Injection Potentiometric Determination of Creatinine in Human Serum", *Electroanalysis,* 2005, v. 17, 2246-2253.

Ballester P. "Switching from Separated to Contact Ion-Pair Binding Modes with Diastereomeric Calix[4]pyrrole Bisphosphonate Receptors", J. Am. Chem. Soc., 2012, v. 134, 13121-13132.

Bakker E., et al., "Carrier-Based Ion-Selective Electrodes and Bulk Optodes. 1. General Characteristics" Pretsch Chem. Rev., 1997, v. 97, 3083-3132.

Tanji yin and wei qin, "Applications of nanomaterials in potentiometric sensors", Trends in Analytical Chemistry, 2013, 51, 79-86.

Umezawa et al., "Applications of nanomaterials in potentiometric sensors", Pure Appl. Chem. 2000, 72, 1851-2082.

Galán A. et al., "Synthesis, structure, and binding properties of lipophilic cavitands based on a calix[4]pyrrole-resorcinarene hybrid scaffold", J. Org. Chem., 2014, 79, 5545-5557.

The invention claimed is:

1. An ionophore compound for creatinine quantification, the compound having a formula of formula (Ia), or alternatively (Ib) or alternatively (Ic), or any of the stereoisomers of (Ia), (Ib) or (Ic):

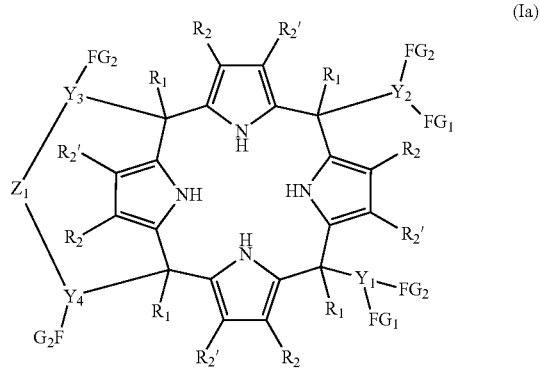

(Ia)

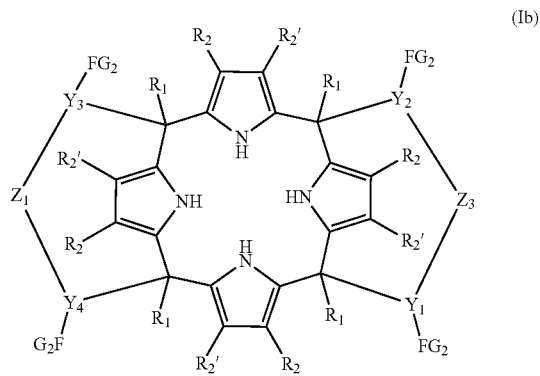

(Ib)

-continued

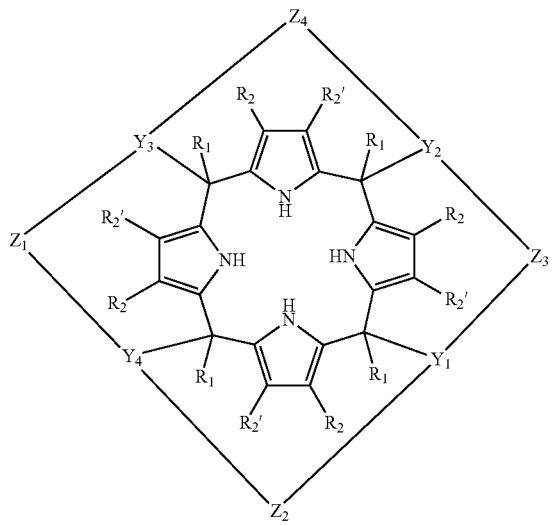
(Ic)

wherein:
R1 is a monoradical selected from the group consisting of hydrogen; (C1-C20)alkyl; (C3-C20)alkenyl; (C3-C20)alkynyl; (C1-C6)alkyl-O—; (C1-C20)haloalkyl; (C6-C20)aryl; (C6-C20)aryl substituted with one or more radicals independently selected from (C1-C20)alkyl, (C1-C6)alkyl-O—, (C1-C6)haloalkyl, halogen, cyano, and nitro; (C6-C20)heteroaryl; and (C6-C20)heteroaryl substituted with one or more radicals independently selected from (C1-C20)alkyl, (C1-C6)alkyl-O—, (C1-C6)haloalkyl, halogen, cyano, and nitro;

R2, and R2' are monoradicals each one being independently selected from the group consisting of hydrogen, (C1-C20)alkyl, (C1-C6)alkyl-O—, (C1-C6)haloalkyl, halogen, cyano, and nitro; and Z1 to Z4 are diradicals of formula (III)

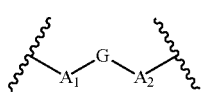
(III)

wherein A1 and A2 are independently selected from the group consisting of O— and —NR3-, wherein R3 is selected from the group consisting of hydrogen and (C1-C20)alkyl; and G is a diradical selected from the group consisting of —NH$_2$, —P(=S)(R5), S(=O)$_2$—, (C1-C6)alkyl, S(=O)—, C(=O)—, —P(=O)(R4)-, —P(=O)(NR6R7)- and P(=O)(OR4);

R4 and R5 are monoradicals independently selected from the group consisting of (C1-C20)alkyl; (C3-C8)cycloalkyl; (C2-C20)alkenyl; (C3-C20)cycloalkyl; (C1-C20)haloalkyl; (C1-C20)alkyl-O—; (C6-C20)aryl; (C6-C20)heteroaryl; (C6-C20)aryl substituted with one or more radicals independently selected from (C1-C20)alkyl, (C1-C6)haloalkyl, (C1-C6)alkyl-O—, halogen, cyano, nitro; and (C6-C20)heteroaryl substituted with one or more radicals independently selected from (C1-C20)alkyl, (C1-C6)alkyl-O—, (C1-C6)haloalkyl, halogen, cyano, and nitro;

Y1 to Y4 are triradicals each one independently selected from the group consisting of (C1-C8)alkyl; (C3-C7)cycloalkyl; (C6-C20)aryl; (C6-C20)aryl substituted with one or more radicals independently selected from the group consisting of: (C1-C20)alkyl, (C1-C6)alkyl-O—, (C1-C6)haloalkyl, halogen, cyano, and nitro; (C6-C20)heteroaryl; and (C6-C20)heteroaryl substituted with one or more radicals independently selected from the group consisting of: (C1-C20)alkyl, (C1-C6)alkyl-O—, (C1-C6)haloalkyl, halogen, cyano, and nitro;

R6 and R7 are monoradicals independently selected from the group consisting of —H and (C1-C20)alkyl;

FG1 and FG2 are —OH; and NHR8 wherein R8 is a radical selected from the group consisting of hydrogen and (C1-C20)alkyl;

wherein:
(C6-C20)aryl represents a ring system from 6 to 20 carbon atoms, the system comprising from 1 to 3 rings, where each one of the rings forming the ring system: is saturated, partially unsaturated, or aromatic; and is isolated, partially fused or totally fused;

(C6-C20)heteroaryl represents a C— radical of a ring system from 6 to 20 members, the system comprising from 1 to 3 rings, wherein at least one of the rings contains from one to four heteroatoms independently selected from O, S and N, and wherein each one of the rings forming the ring system: is saturated, partially unsaturated or aromatic; and is isolated, partially fused or totally fused; and (C3-C20)cycloalkyl refers to a saturated carbocyclic ring containing from 3 to 7 carbon atoms.

2. An ionophore compound for creatinine quantification, the compound having a formula of:

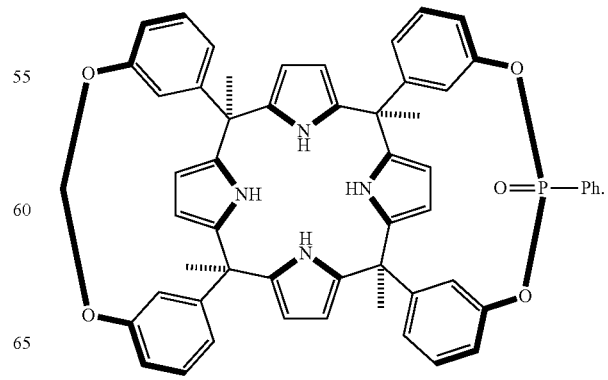

3. An ionophore compound for creatinine quantification, the compound having a formula of:
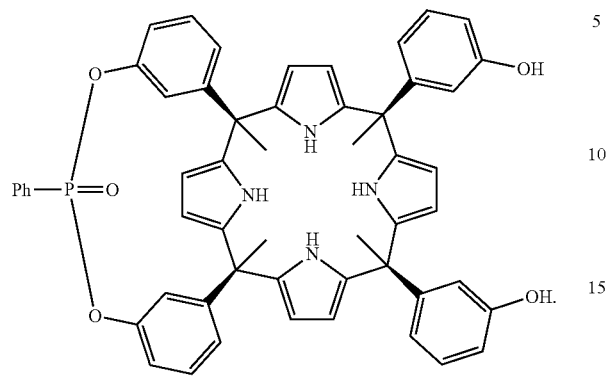
* * * * *